(12) United States Patent
Liphardt et al.

(10) Patent No.: US 7,245,376 B2
(45) Date of Patent: *Jul. 17, 2007

(54) COMBINED SPATIAL FILTER AND RELAY SYSTEMS IN ROTATING COMPENSATOR ELLIPSOMETER/POLARIMETER

(75) Inventors: Martin M. Liphardt, Lincoln, NE (US); Blaine D. Johs, Lincoln, NE (US); Jeffrey S. Hale, Lincoln, NE (US); Craig M. Herzinger, Lincoln, NE (US); Steven E. Green, Lincoln, NE (US); Ping He, Lincoln, NE (US); John A. Woollam, Lincoln, NE (US)

(73) Assignee: J. A. Woollam Co., Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/284,213

(22) Filed: Nov. 22, 2005

(65) Prior Publication Data

US 2006/0268272 A1 Nov. 30, 2006

Related U.S. Application Data

(63) Continuation-in-part of application No. 11/085,450, filed on Mar. 22, 2005, which is a continuation-in-part of application No. 10/928,429, filed on Aug. 27, 2004, application No. 11/284,213, which is a continuation-in-part of application No. 11/103,229, filed on Apr. 12, 2005, now Pat. No. 7,215,424, and a continuation-in-part of application No. 10/699,540, filed on Nov. 1, 2003, now Pat. No. 7,158,231, which is a continuation-in-part of application No. 10/034,800, filed on Dec. 28, 2001, now Pat. No. 6,822,738, which is a continuation-in-part of application No. 09/945,962, filed on Sep. 4, 2001, now Pat. No. 7,075,649, and a continuation-in-part of application No. 09/946,011, filed on Feb. 1, 2000, now Pat. No. 6,353,477, which is a continuation-in-part of application No. 09/246,888, filed on Feb. 8, 1999, now Pat. No. 6,084,675, which is a continuation-in-part of application No. 08/912,211, filed on Aug. 15, 1997, now Pat. No. 5,872,630, which is a continuation-in-part of application No. 08/618,820, filed on Mar. 20, 1996, now Pat. No. 5,706,212, and a continuation-in-part of application No. 08/530,892, filed on Sep. 20, 1995, now Pat. No. 5,666,201, application No. 11/284,213, which is a continuation-in-part of application No. 10/829,620, filed on Apr. 22, 2004, now Pat. No. 7,193,710.

(60) Provisional application No. 60/576,466, filed on Jun. 3, 2004, provisional application No. 60/498,479, filed on Aug. 28, 2003, provisional application No. 60/473,615, filed on May 28, 2003, provisional application No. 60/437,023, filed on Dec. 31, 2002, provisional application No. 60/427,043, filed on Nov. 18, 2002, provisional application No. 60/424,589, filed on Nov. 7, 2002.

(51) Int. Cl.
*G01J 4/00* (2006.01)

(52) U.S. Cl. ..................................... 356/369

(58) Field of Classification Search ............. 356/369
See application file for complete search history.

(56) References Cited

U.S. PATENT DOCUMENTS 548,495 A 10/1895 Abbe (Continued)

OTHER PUBLICATIONS

WO 01/90687 A2, Thermawave.

(Continued)

*Primary Examiner*—Tarifur Chowdhury
*Assistant Examiner*—Isiaka O. Akanbi
(74) *Attorney, Agent, or Firm*—James D. Welch

(57) ABSTRACT

Low aberration relay systems modified to perform as spatial filters in rotating compensator ellipsometer, polarimeter and the like systems.

33 Claims, 15 Drawing Sheets

U.S. PATENT DOCUMENTS

| | | | | |
|---|---|---|---|---|
| 2,447,828 A | 8/1948 | West | | 359/495 |
| 3,748,015 A | 7/1973 | Offner | | 359/366 |
| 3,817,624 A | 6/1974 | Martin | | 356/138 |
| 4,053,232 A | 10/1977 | Dill et al. | | 356/118 |
| 4,054,812 A | 10/1977 | Lessner et al. | | 313/44 |
| 4,176,951 A | 12/1979 | Robert et al. | | 356/33 |
| 4,179,217 A | 12/1979 | Robert et al. | | 356/33 |
| 4,322,165 A | 3/1982 | Ellebracht et al. | | 356/316 |
| 4,556,292 A | 12/1985 | Mathyssek et al. | | 350/394 |
| 4,668,086 A | 5/1987 | Redner | | 356/33 |
| 4,770,895 A | 9/1988 | Hartley | | 427/10 |
| 4,772,104 A | 9/1988 | Buhrer | | 350/403 |
| 4,875,773 A | 10/1989 | Burns et al. | | 356/328 |
| 4,917,461 A | 4/1990 | Goldstein | | 350/286 |
| 4,961,634 A | 10/1990 | Chipman | | 350/403 |
| 5,016,980 A | 5/1991 | Waldron | | 350/286 |
| 5,091,320 A | 2/1992 | Aspnes et al. | | 427/8 |
| 5,166,752 A | 11/1992 | Spanier et al. | | 356/369 |
| 5,229,833 A | 7/1993 | Stewart | | 356/352 |
| 5,329,357 A | 7/1994 | Bernoux et al. | | 356/369 |
| 5,373,359 A | 12/1994 | Woollam et al. | | 356/328 |
| 5,475,525 A | 12/1995 | Tournois et al. | | 359/245 |
| 5,504,582 A | 4/1996 | Johs et al. | | 356/369 |
| 5,521,706 A | 5/1996 | Green et al. | | 356/369 |
| 5,581,350 A | 12/1996 | Chen et al. | | 356/369 |
| 5,596,406 A | 1/1997 | Rosencwaig et al. | | 356/327 |
| 5,608,526 A | 3/1997 | Piwonka-Corle et al. | | 356/369 |
| 5,666,201 A | 9/1997 | Johs | | 356/369 |
| 5,706,212 A | 1/1998 | Thompson et al. | | 364/525 |
| 5,713,364 A | * | 2/1998 | DeBaryshe et al. | 600/476 |
| 5,793,480 A | 8/1998 | Lacey et al. | | 356/73 |
| 5,818,596 A | 10/1998 | Imai et al. | | 356/630 |
| 5,859,424 A | * | 1/1999 | Norton et al. | 250/226 |
| 5,872,630 A | 2/1999 | Johs et al. | | 356/369 |
| 5,877,859 A | 3/1999 | Aspnes et al. | | 356/364 |
| 5,910,842 A | 6/1999 | Piwonka-Corle et al. | | 356/369 |
| 5,917,594 A | 6/1999 | Norton | | 356/327 |
| 5,929,995 A | 7/1999 | Johs | | 356/369 |
| 5,946,098 A | 8/1999 | Johs et al. | | 356/364 |
| 5,963,325 A | 10/1999 | Johs et al. | | 356/364 |
| 5,973,787 A | 10/1999 | Aspnes et al. | | 356/369 |
| 6,031,619 A | 2/2000 | Wilkens et al. | | 356/419 |
| 6,034,777 A | 3/2000 | Johs et al. | | 356/369 |
| 6,084,674 A | 7/2000 | Johs et al. | | 356/364 |
| 6,084,675 A | 7/2000 | Herzinger et al. | | 356/369 |
| 6,100,981 A | 8/2000 | Johs et al. | | 356/364 |
| 6,118,537 A | 9/2000 | Johs et al. | | 356/369 |
| 6,134,012 A | 10/2000 | Aspnes et al. | | 356/369 |
| 6,141,102 A | 10/2000 | Johs et al. | | 356/364 |
| 6,181,421 B1 | 1/2001 | Aspnes et al. | | 356/369 |
| 6,320,657 B1 | 11/2001 | Aspnes et al. | | 356/369 |
| 6,353,477 B1 | * | 3/2002 | Johs et al. | 356/369 |
| 6,414,302 B1 | 7/2002 | Freeouf | | 250/225 |
| 6,493,097 B1 | 12/2002 | Ivarsson | | 356/630 |
| 6,545,758 B1 | * | 4/2003 | Sandstrom | 356/317 |
| 6,587,282 B1 | * | 7/2003 | Wang et al. | 359/797 |
| 6,734,967 B1 | 5/2004 | Piwonka-Corle et al. | | 356/369 |
| 6,822,738 B1 | * | 11/2004 | Johs et al. | 356/369 |
| 2002/0101587 A1 | * | 8/2002 | Wilson et al. | 356/328 |
| 2002/0149774 A1 | 10/2002 | McAninch | | |
| 2003/0071996 A1 | 4/2003 | Wang et al. | | |
| 2003/0150997 A1 | 8/2003 | Eckert et al. | | |
| 2005/0286047 A1 | * | 12/2005 | Boege | 356/317 |

OTHER PUBLICATIONS

WO 01/086257.
J.A. Woollam Co. Flyer on VUV-VASE.

* cited by examiner

FIG. 6a
FIG. 6B
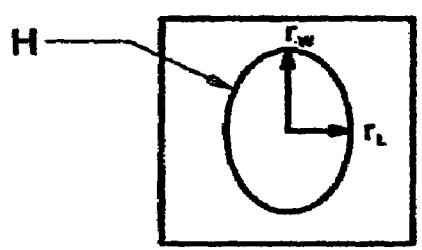
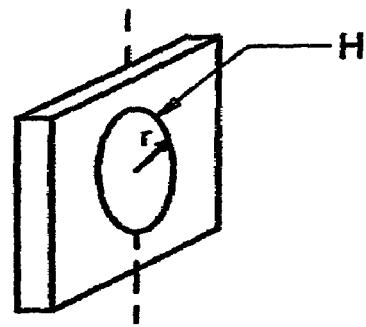
FIG. 6c
FIG. 6d

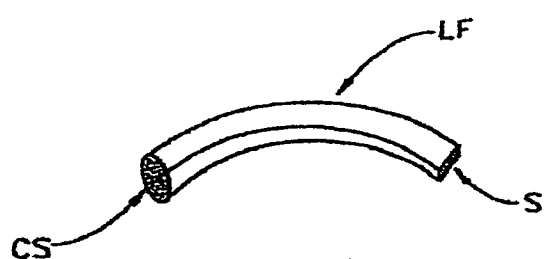
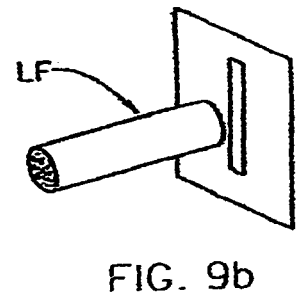
FIG. 9a    FIG. 9b
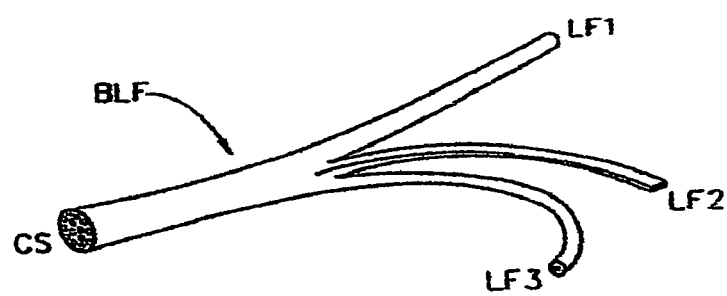
FIG. 9c
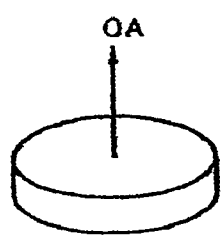
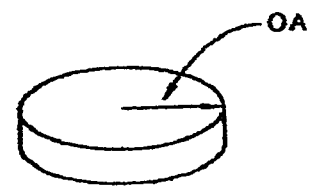
FIG. 9d    FIG. 9e
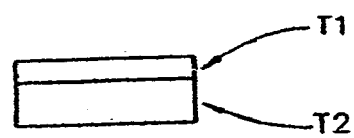
FIG 9f

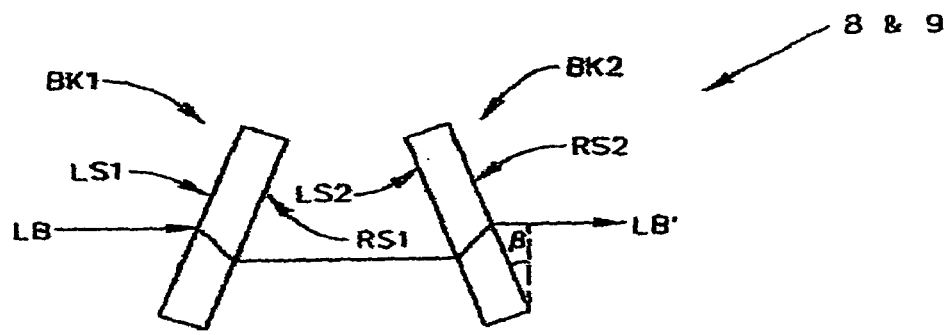
FIG. 9o1
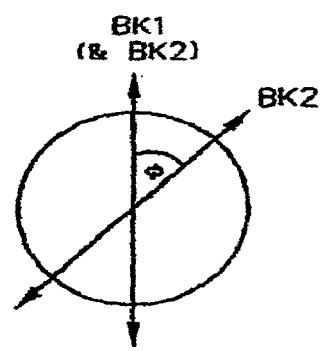
FIG. 9o2
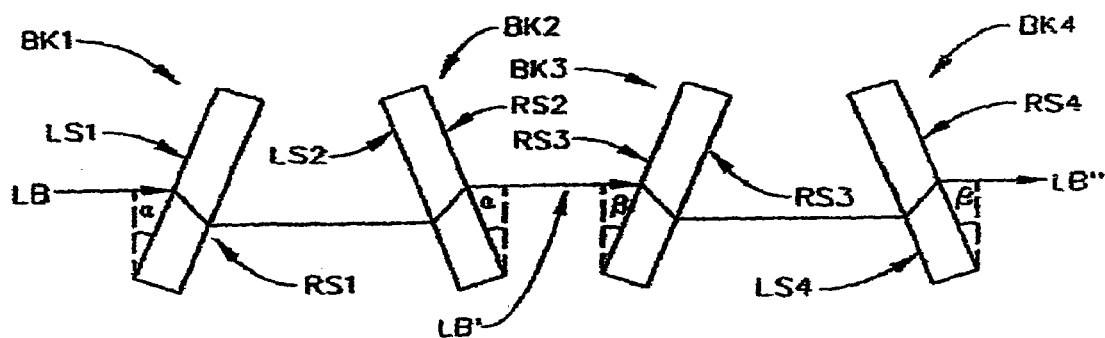
FIG. 9p1

FIG. 9p2

COMBINED SPATIAL FILTER AND RELAY SYSTEMS IN ROTATING COMPENSATOR ELLIPSOMETER/POLARIMETER

This application is a CIP of application Ser. No. 11/085,450 Filed Mar. 22, 2005, which is a continuation-in-part of Ser. No. 10/928,429, Filed Aug. 27, 2004 and which Claims Benefit of Provisional Application 60/498,479 Filed Aug. 28, 2003. Further, Benefit of Provisional Application Ser. No. 60/576,466 Filed Jun. 3, 2004 is Claimed directly. This Application is also a CIP of application Ser. No. 11/103,229 Filed Apr. 12, 2005, now U.S. Pat. No 7,215,424, and of application Ser. No. 10/699,540 Filed Nov. 1, 2003, now U.S. Pat. No. 7,158,231, which is a continuation-in-part of application Ser. No. 10/034,800 FILED Dec. 28, 2001 now U.S. Pat. No. 6,822,738; which is a continuation-in-part of: Ser. No. 09/945,962 filed Sep. 4, 2001 now U.S. Pat. No. 7,075,649, and Ser. No. 09/496,011 filed Feb. 1, 2000, (now U.S. Pat. No. 6,353,477); which is a CIP of Ser. No. 09/246,888 filed Feb. 8, 1999 (U.S. Pat. No. 6,084,675), which is a CIP of Ser. No. 08/912,211 filed Aug. 15, 1997 (U.S. Pat. No. 5,872,630), which is a CIP of Ser. No. 08/530,892 filed Sep. 20, 1995 (U.S. Pat. No. 5,666,201); and is a CIP of Ser. No. 08/618,820 filed Mar. 20, 1996 (U.S. Pat. No. 5,706,212). This Application also is a CIP of application Ser. No. 11/103,229 Filed Apr. 12, 2005 and of Ser. No. 10/829,620 Filed Apr. 22, 2004 now U.S. Pat. No. 7,193,710. This Application also Claims Benefit of Provisional Applications: 60/473,615 Filed May 28, 2003; 60/437,023 Filed Dec. 31, 2002; 60/424,589 Filed Nov. 7, 2002 and 60/427,043 Filed Nov. 18, 2002.

TECHNICAL FIELD

The disclosed invention relates to spatial filters, and more particularly to low aberration relay systems modified to perform as spatial filters in rotating compensator ellipsometers.

BACKGROUND

Ellipsometry is a well known means by which to monitor material systems, (samples). In brief, a polarized beam of electromagnetic radiation of one or more wavelengths is caused to impinge upon a material system, (sample), along one or more angles of incidence and then interact with a material system, (sample). Beams of electromagnetic radiation can be considered as comprised of two orthogonal components, (ie. "P" and "S"), where "P" identifies a plane which contains both an incident beam of electromagnetic radiation, and a normal to an investigated surface of a material system, (sample), being investigated, and where "S" identifies a plane perpendicular to the "P" plane and parallel to said surface of said material system, (sample). A change in polarization state in a polarized beam of electromagnetic radiation caused by said interaction with a material system, (sample), is representative of properties of said material system, (sample). (Note Polarization State basically refers to a magnitude of a ratio of orthogonal component magnitudes in a polarized beam of electromagnetic radiation, and a phase angle therebetween.) Generally two well known angles, (PSI and DELTA), which characterize a material system, (sample), at a given Angle-of-Incidence, are determined by analysis of data which represents change in polarization state. Additional sample identifying information is often also obtained by application of ellipsometry, including layer thicknesses, (including thicknesses for multilayers), optical thicknesses, sample temperature, refractive indicies and extinction coefficients, index grading, sample composition, surface roughness, alloy and/or void fraction, parameter dispersal and spectral dependencies on wavelength, vertical and lateral inhomogenieties etc.

Continuing, Ellipsometer Systems generally include a source of a beam of electromagnetic radiation, a Polarizer means, which serves to impose a linear state of polarization on a beam of electromagnetic radiation, a Stage for supporting a material system, (sample), and an Analyzer means which serves to select a polarization state in a beam of electromagnetic radiation after it has interacted with a material system, (sample), and pass it to a Detector System for analysis therein. As well, one or more Compensator(s) can be present and serve to affect a phase angle change between orthogonal components of a polarized beam of electromagnetic radiation.

A number of types of ellipsometer systems exist, such as those which include rotating elements and those which include modulation elements. Those including rotating elements include Rotating Polarizer (RP), Rotating Analyzer (RA) and Rotating Compensator (RC). The presently disclosed invention comprises a Rotating Compensator Ellipsometer System. It is noted that Rotating Compensator Ellipsometer Systems do not demonstrate "Dead-Spots" where obtaining data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees. The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

Continuing, it is known in the art to focus a broadband beam of electromagnetic radiation onto a small spot in ellipsometers by reflective or refractive optics. Typically, said prior art systems image a small aperture onto a spot on a sample with high demagnification, and suffer from varying degrees of optical aberrations, (eg. spherical, chromatic, astigmatism etc.). Further, surfaces of mirrors can be non-ideal as a result of non-traditional manufacturing of special optics. Further, the cost of non-spherical optics is high.

A Search for relevant patents provided expired U.S. Pat. No. 3,748,015, to Offner, which reveals that it is known that spherical optics can be fashioned to relay an objective with 1:1 magnification and with essentially no aberrations. Said expired U.S. Pat. No. 3,748,015, to Offner, describes such a relay system comprising two elements:

a) a concave spherical mirror; and c) a convex spherical mirror;

said elements being arrange such that electromagnetic radiation caused to approach the concave spherical reflects at a first location thereon is reflected to said a convex spherical mirror, from which it reflects onto a second location of said concave spherical mirror, from which it reflects as a converging beam of electromagnetic radiation if the electromagnetic radiation caused to approach the concave spherical mirror at a first location was, for instance, a point source. FIG. 1 of this disclosure demonstrates a 015 patent System.

Patents which describe reflective optics in ellipsometer systems are U.S. Pat. Nos. 6,734,967; 5,910,842 and 5,608,526 to Piwonka-Corle et al. The 526 patent is the earliest thereof to describe use of all-reflective focusing elements in an ellipsometer. U.S. Pat. Nos. 5,859,424 and 5,917,594 to Norton, are disclosed as they describe use of an apodizing filter to decrease beam spot size on a sample, and use of a negative miniscus lens to correct for spherical abberations where a spherical mirror is present in the path of an electromagnetic beam.

An important U.S. Pat. Ser. No. 5,872,630, is that to Johs et al., from which the present application is derived as a CIP via intervening CIP applications. Said 630 patent describes:

A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
  before said stage for supporting a material system;
  after said stage for supporting a material system; and
  both before and after said stage for supporting a material system;
such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system.

Said 630 patent also, amongst other disclosure, describes a Mathematical Regression based Calibration procedure which makes possible the use of essentially any compensator regardless of non-achromatic characteristics.

Another patent to Johs, from which the 630 patent was Continued-in Part, is U.S. Pat. No. 5,666,201, filed Sep. 20, 1995. The focus in said 201 patent comprises a detector arrangement in which multiple orders of a dispersed beam of electromagnetic radiation are intercepted by multiple detector systems. However, Claim 8 in the 201 patent, in combination with a viewing the Drawings therein, provide conception of the Spectroscopic Rotating Compensator Ellipsometer, as Claimed in Claim 1 of the JAW 630 patent and, in fact, the the 630 patent issued in view of a Terminal Disclaimer based upon the 201 patent. A CIP of the 630 patent, is U.S. Pat. No. 6,353,477 to Johs et al. which describes prefered multiple element compensators.

Also disclosed is U.S. Pat. No. 5,706,212, Issued Jan. 6, 1998, and Filed Mar. 20, 1996 for an Infrared Ellipsometer System Regression based Calibration Procedure. Said 212 patent describes use of an Substantially Achromatic Rotating Compensator and application of Mathematical Regression in a Calibration procedure which evaluates calibration parameters in both rotating and stationary components. The 212 patent describes that 2 OMEGA and 4 OMEGA associated terms are generated by a detector of a signal which passes through a compensator caused to rotate at a rate of OMEGA. Said 630 patent was Continued-in-Part therefrom, as is the present application via an intervening patent application. It is noted that the 212 patent application was filed four months prior to the earliest priority patent application, of Aspnes et al. (ie. U.S. Pat. Nos. 6,320,657 B1, 6,134,012, 5,973,787 and 5,877,859), the later of which was Filed on Jul. 24, 1996.

Relevant patents to Aspnes et al. are U.S. Pat. Nos. 6,320,657 B1, 6,134,012, 5,973,787 and 5,877,859. These patents describe a Broadband Spectroscopic Rotating Compensator Ellipsometer System wherein the Utility is found in the use of a "substantially Non-Achromatic" compensator, (see Claim 1 in the 657 patent), and selecting a Wavelength Range and Compensator so that "an effective phase retardation value is induced covering at least from 90 degrees to 180 degrees", (012 patent), over a range of wavelengths of at least 200-800 nm. The 787 and 859 recite that at least one wavelength in said wavelength Range has a retardation imposed of between 135 and 225 Degrees, and another wavelength in the wavelength Range has a retardation imposed which is outside that retardation Range. The Utility of the Therma-wave patents derives from the identified conditions being met so that at least one of a 2 OMEGA and a 4 OMEGA coefficient provided by a detector provides usable information at a wavelength, even when said coefficient does not provide usable information at other wavelengths. Again, the identified Aspnes et al. patents recite directly, or describe the presence of a "substantially-non-Achromatic" compensator, while, it is noted at this point, the invention disclosed in this application utilizes what are properly termed substantially-achromatic or Psuedo-Achromatic compensators. It is further noted that the U.S. Pat. No. 5,716,212 patent application, from which this Application Continues-in-Part, was filed prior to Jul. 24, 1976 filing date of the 859 Aspnes et al. priority patent application. The disclosed invention then has Priority to simultaneous use of 2 OMEGA and 4 OMEGA signals provided from a detector in a spectroscopic rotating compensator ellipsometer system which utilizes "Other-Than-Substantially Non-Achromatic" Compensators, namely "Substantially-Achromatic" or "Pseudo-Achromatic" Compensators, to characterize samples, emphasis added.

A recently published PCT application is No. WO 01/90687 A2, which is based on U.S. application Ser. No. 09/575,295 filed May 3, 2001. This Application was filed by Thermawave Inc. and specifically describes separate use of a $2\omega$ and a $4\omega$ term to provide insight to sample thickness and temperature.

Another, U.S. Pat. No. 4,053,232 to Dill et al. describes a Rotating-Compensator Ellipsometer System, which operates utilizes monochromatic light.

Two patents which identify systems which utilize Polychromatic light in investigation of material systems, U.S. Pat. Nos. 5,596,406 and 4,668,086 to Rosencwaig et al. and Redner, respectively, were also identified.

Also identified is a patent to Woollam et al, U.S. Pat. No. 5,373,359 as it describes a Rotating Analyzer Ellipsometer System which utilizes white light. Patents continued from the 359 Woollam et al. are, U.S. Pat. No. 5,504,582 to Johs et al. and U.S. Pat. No. 5,521,706 to Green et al. Said 582

Johs et al. and 706 Green et al. Patents describe use of polychromatic light in a Rotating Analyzer Ellipsometer System.

A U.S. Pat. No. 6,034,777 to Johs et al., describes application of ellipsometry in an evacuated chamber comprising windows.

A U.S. Pat. No. 5,929,995 to Johs, is disclosed as it describes application of ellipsometry in an evacuated chamber comprising windows.

A U.S. Pat. No. 5,329,357 to Bernoux et al., is identified as it describes the use of optical fibers as input and output means in an ellipsometer system.

A U.S. Pat. No. 5,581,350 to Chen et al., is identified as it describes the application of regression in calibration of ellipsometer systems.

Additionally, patents pertaining to optical elements, and particularly to compensators/retarders per se are:

U.S. Pat. No. 4,917,461 to Goldstein, describes an achromatic infrared retarder comprised of two identical prisms in combination with a rflective surface;

U.S. Pat. No. 4,772,104 to Buhrer which describes an achromatic optical filter comprised of two birefringent disks;

U.S. Pat. No. 4,961,634 to Chipman describes an infrared achromatic retarder comprised of CdS and CdSe plates aligned with the fast axes thereof perpendicular to one another;

U.S. Pat. No. 6,181,421 to Aspnes et al., describes a tipped Berek Plate Compensator.

U.S. Pat. No. 5,946,098 to Johs, Herzinger and Green, describes numerous optical elements. In addition U.S. Pat. Nos. 6,084,674; 6,118,537; 6,100,981; 6,141,102; 6,100,981; 5,963,325; 6,084,674 to Johs et al. and to Herzinger et al. U.S. Pat. No. 6,084,675, which applications depend from application Ser. No. 08/997,311 filed Dec. 23, 1997, now said U.S. Pat. No. 5,946,098;

Additional patents which describe Compensators are U.S. Pat. No. 548,495 to Abbe; U.S. Pat. No. 4,556,292 to Mathyssek et al.; U.S. Pat. No. 5,475,525 Tournois et al.; U.S. Pat. No. 5,016,980 Waldron; and U.S. Pat. No. 3,817,624 to Martin and U.S. Pat. No. 2,447,828 to West;

And, U.S. Pat. Nos. 4,176,951 and 4,179,217 to Robert et al., are also disclosed as they describe rotating Birefringent elements in Ellipsometers which produce 2 and 4 components.

A PCT patent application, No. WO 01/086257 is also known and is disclosed as it describes a combination of an aperture and lens to define a spot on a sample.

A U.S. Pat. No. 5,793,480 to Lacey et al., is disclosed as it describes a field stop and lens combination in an ellipsometer prior to a sample.

A U.S. Pat. No. 5,166,752 to Spanier et al., is disclosed as it describes an ellipsometer with lenses and apertures before and after a sample.

A U.S. Pat. No. 4,054,812 to Lessner et al., describes a Source of Spectroscopic electromagetnic radiation which provides heat sink and ozone containment.

A U.S. Pat. No. 4,322,165 to Ellebracht et al., is disclosed as it decribes purging in a VUV Plasma Atomic Emission Spectroscopic Instrument.

A U.S. Pat. No. 4,875,773 to Burns et al., is disclosed as it describes an Optical System for a Multidetector Array Spectrograph.

A U.S. Pat. No. 6,414,302 to Freeouf, is disclosed as it describes a High Photon Energy, (up through 10 eV), Range Reflected Light Characterization System.

A U.S. Pat. No. 5,091,320 to Aspnes et al., is disclosed as it describes application of ellipsometry with an evacuated chamber.

A U.S. Pat. No. 4,770,895 to Hartley, is disclosed as it describes application of ellipsometry with an evacuated chamber.

A Published Patent Application by McAninch, No, 2002/0149774 A1 is disclosed as it describes purging a measurement region near a substrate in a metrology tool.

A J. A. Woollam CO. Flyer titled VUV-VASE (Registered Trademark), is disclosed as it describes a monochromater based rotating analyzer ellipsomete system in a purged chamber.

A U.S. Pat. No. 6,493,097 to Ivarsson, is disclosed as it describes a Detector Array in an analytical instrument using electromagnetic radiation.

A U.S. Pat. No. 5,229,833 to Stewart, is disclosed as it describes an optical sensor comprising a CCD Array.

A U.S. Pat. No. 5,337,146 to Azzam, is disclosed as it describes a spectrophotometer comprising a linear array detector.

A U.S. Pat. No. 6,031,619 to Wilkins et al., describes an imaging spectrometer with a CCD Matrix or Row detector.

A U.S. Pat. No. 5,818,596 to Imai et al., is disclosed as it describes use of purging gas to prevent contaminants on samples, but does not disclose ellipsometry or a multiple detector element detector aray.

A Published Patent Application by McAninch, No, 2002/0149774 A1 is disclosed as it describes purging a measurement region near a substrate in a metrology tool.

A Published Patent Application by Wang et al., No. 2003/0071996 A1 is disclosed as it involves purging of the environment of one beam in a system involving two beams.

A Published Patent Application by Eckert et al., No. US 2003/0150997 A1 is disclosed as it describes use of VUV wavelengths and purging.

A recent U.S. Pat. No. 6,940,596 to Uhrich et al., describes a three element focusing lens in a spectroscopic ellipsometer, in which the lenses are two convex calcium fluoride lenses disposed on opposite sides of a fused silica lens.

Regarding Articles,

An article by Johs, titled "Regression Calibration Method For Rotating Element Ellipsometers", which appeared in Thin Film Solids, Vol. 234 in 1993 is also identified as it predates the Chen et al. patent and describes an essentially similar approach to ellipsometer calibration.

An Article titled "A New Purged UV Spectroscopic Ellipsometer to Characterize Thin Films and Multilayers at 157 nm", Boher et al., Proc. SPIE, Vol. 3998, (June 2000) is disclosed as it describes a UV Spectroscopic Ellipsometer in combination with Purging.

A presentation titled "Characterisation of Thin Films and Multilayers in the VUV Wavelength Range Using Spectroscopic Ellipsometry and Spectroscopic Photometry", Boher et al., 157 nm Symposium, May 2000) is disclosed as it describes a UV Spectroscopic Ellipsometer.

A paper titled "Progress in Spectroscopic Ellipsometry: Applications from Ultraviolet to Infrared", Hilfiker et al., J. Vac. Sci. Technol. A, (July/August 2003).

A paper titled "Atomic Scale Characterization of Semiconductors by In-Situ Real Time Spectroscopic Ellipsometry", Boher et al., Thin Solid Films 318 (1998) is disclosed as it mentions multichannel detectors.

A paper titled "Optical Characterization in the Vacuum Ultraviolet with Variable Angle Spectroscopic Ellipsometry:

157 nm and below", Hilfiker et al., Proc. SPIE Vol. 3998 (2000) is disclosed as it describes use of the J.A. Woollam CO. VUV-VASE which is a monochromater based purged system.

A paper titled "Feasibility and Applicability of Integrated Metrology Using Spectroscopic Ellipsometry in a Cluster Tool", Boher et al., SPIE Vol. 4449, (2001) is disclosed as it describes a multichannel ellipsometer applied outside an environmental chamber. This application required electromagnetic radiation to pass through windows to reach a sample.

Four papers authored or co-authored by Collins, which describe use of multichannels and rotating element ellipsometers, including rotating compensator, but not in an environmental chamber are:

"Characterization of Wide Bandgap Thin Film Growth Using UV-Extended Real Time Spectroscopic Ellipsometry Applications to Cubic Boron Nitride", Zapien et al., J. of Wide Bandgap Materials, Vol 9, No. 3 (January 2002);

"Automated Rotating Element Ellipsometers: Calibration, Operation, and Real-Time Applications", Collins, Rev. Sci. Instrum. 61 (8) (August 1990);

"Waveform Analysis With Optical Multichannel Detectors: Applications for Rapid-Scan Spectroscopic Ellipsometers", An et al., Rev. Sci. Instrum. 62(8), (August 1991); and "Multichannel Ellipsometer for Real Time Spectroscopy of Thin Film Deposition for 1.5 to 6.5 eV", Zapien et al., Rev. Sci. Instrum. Vol. 71, No. 9, (September 1991).

A book by Azzam and Bashara titled "Ellipsometry and Polarized light" North-Holland, 1977 is disclosed and incorporated herein by reference for general theory.

As well, identified for authority regarding regression, is a book titled Numerical Recipes in "C", 1988, Cambridge University Press.

The disclosed invention applies the system of the expired 015 patent in reflectometer, spectrophotometer, ellipsometer, polarimeter and the like systems, variously combined with spatial filters.

DISCLOSURE OF THE INVENTION

To begin, it is first disclosed that the present invention is primarily a spectroscopic rotating compensator material system investigation system comprising a source of polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
  before said stage for supporting a material system;
  after said stage for supporting a material system; and
  both before and after said stage for supporting a material system;

as Claimed in Parent U.S. Pat. No. 5,872,630, to Johs, from which this Application is a CIP. The improvement Claimed herein is the inclusion of combined spatial filter and relay system for providing a small spot of electromagnetic radiation at a material system.

One embodiment of the disclosed invention combined spatial filter and relay system comprises three elements:
  a) a concave spherical mirror having at least one concave spherical surface and an aperture hole therethrough;
  b) a flat mirror; and
  c) a convex spherical mirror having at least one convex spherical surface.

Said elements are arranged such that electromagnetic radiation caused to approach the concave spherical mirror passes through said aperture hole and reflects from said flat mirror onto a first location of a concave surface of said concave spherical mirror. It then reflects from said first location onto a convex spherical surface of said convex spherical mirror and reflects therefrom onto a second location of said concave surface of said concave spherical mirror from which it reflects as a converging beam of electromagnetic radiation.

A second embodiment of the disclosed combined spatial filter and relay system comprises:
  a) an aperture;
  b) a flat mirror;
  c) a concave spherical mirror having at least one concave spherical surface; and
  d) a convex spherical mirror having at least one convex spherical surface.

Said elements are arranged such that electromagnetic radiation which relay said aperture is caused to approach the flat mirror and reflect therefrom onto a first location of a concave surface of said concave spherical mirror. It then reflects from said first location onto a convex spherical surface of said convex spherical mirror and reflects therefrom onto a second location of said concave surface of said concave spherical mirror from which it reflects as a converging beam of electromagnetic radiation.

Said embodiment can include a second flat mirror positioned to intercept and reflect electromagnetic radiation reflected from said second location of said concave surface of said concave spherical mirror as a converging beam of electromagnetic radiation. Said modified second embodiment then comprises five elements:
  a) an aperture;
  b) a first flat mirror;
  c) a concave spherical mirror having at least one concave spherical surface;
  d) a convex spherical mirror having at least one convex spherical surface; and
  e) a second flat mirror.

Said elements are arranged such that electromagnetic radiation from said aperture is caused to approach the first flat mirror and reflect therefrom onto a first location of a concave surface of said concave spherical mirror. Said beam reflects from said first location onto a convex spherical surface of said convex spherical mirror and reflects therefrom onto a second location of said concave surface of said concave spherical mirror from which it reflects onto said second flat mirror which is positioned to intercept and reflect electromagnetic radiation reflected from said second location of said concave surface of said concave spherical mirror, as a converging beam of electromagnetic radiation.

In ellipsometry applications it is best to keep the angle of incidence of electromagnetic radiation onto a flat mirror low, (eg. less than 20 degrees). Where it is desired to use a larger angle, say 45 degrees, the presently disclosed invention can be advantageously modified. An example is a system for investigating a material system comprising:

a source of electromagnetic radiation;

an aperture;

first and second relay systems, each thereof comprising four elements:
a) a first flat mirror;
b) a concave spherical mirror having at least one concave spherical surface;
c) a convex spherical mirror having at least one convex spherical surface; and
d) a second flat mirror.

Said elements are arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror, which is positioned to intercept and reflect electromagnetic radiation reflected from said second location of said concave surface of said concave spherical mirror as a converging beam of electromagnetic radiation;

and a detector;

said material system being positioned between said first and second relay systems.

Said first relay system is positioned to relay electromagnetic radiation from the source thereof as it passes through said aperture, and direct it onto a surface of said material system at an oblique angle of incidence, and said second relay system is positioned to receive electromagnetic radiation reflected from the material system and pass it on to said detector, the propagation direction of electromagnetic radiation entering and exiting each of said first and second relay systems being substantially unchanged by passing therethrough.

Said system is further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

(It is noted that while said first and second flat mirrors are typically oriented so that a beam of electromagnetic radiation approaches along a 45 degree Angle-of-Incidence, the present invention is not limited to such a configuration. That is, the Angle-of-Incidence can be any functional angle, where compensating adjustments are made in FIGS. 5a and 5b to effect an intended Angle-of-Incidence of the beam of electromagnetic radiation where it impinges on the Surface of a material system).

A modified system for investigating a material system comprises:

a source of electromagnetic radiation;

an aperture; first and second relay systems, each thereof comprising four elements:
a) a first flat mirror;
b) a concave spherical mirror having at least one concave spherical surface;
c) a convex spherical mirror having at least one convex spherical surface; and
d) a second flat mirror;

said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror, from which it reflects onto said second flat mirror which is positioned to intercept and reflect electromagnetic radiation reflected from said second location of said concave surface of said concave spherical mirror, as a converging beam of electromagnetic radiation;

and a detector;

said first and second relay systems being positioned on the same side of the material system;

the propagation direction of electromagnetic radiation entering and exiting each of said first and second relay systems being substantially unchanged by passing therethrough;

said system being further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

Said system for investigating a material system can further comprises:
a) a polarizer between said source and material system; and
b) an analyzer between said material system and detector;

and constitute an ellipsometer, and if a compensator is present between said source and detector, a polarimeter results.

An additional embodiment of a system for investigating a material system comprises:

a source of electromagnetic radiation;

an aperture;

a relay system comprising three elements:
a) a flat mirror;
b) a concave spherical mirror having at least one concave spherical surface;
c) a convex spherical mirror having at least one convex spherical surface;

said elements being arranged such that electromagnetic radiation is caused to approach the flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects as a converging beam of electromagnetic radiation;

a material system; and a detector.

Said aperture can be in said concave spherical mirror.

Said system for investigating a material system can further comprise:
a) a polarizer between said source and material system; and
b) an analyzer between said material system and detector;

thereby providing an ellipsometer.

There can further be present at least one compensator between said source and detector.

In any of the systems disclosed above, a coating can be present on the surface of at least one present element, (eg. concave, convex, first flat, second flat mirror etc. to change the intensity vs. wavelength plot of a reflected electromagnetic beam relative to an incident beam.

In any of the systems disclosed above said aperture can be circular or actually or effectively non-circular.

As mentioned, the disclosed invention comprises a spectroscopic rotating compensator material system investigation system comprising a source of polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
  before said stage for supporting a material system;
  after said stage for supporting a material system; and
  both before and after said stage for supporting a material system.

A prefered embodiment includes, in the path of said polychromatic beam of electromagnetic radiation, at least four apertures between said source of polychromatic beam of electromagnetic radiation and said stage for supporting a material system, and at least three apertures between said stage for supporting a material system and said at least one detector system. When said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said at least one compensator(s) and said at least four apertures between said source of a polychromatic beam of electromagnetic radiation and said stage for supporting a material system. Said polychromatic beam of electromagnetic radiation is then caused to interact with a material system on said stage for supporting a material system, pass through said analyzer and said at least three apertures between said stage for supporting a material system, and interact with said dispersive optics such that a multiplicity of essentially single wavelengths are caused to simultaneously enter a corresponding multiplicity of detector elements in said at least one detector system.

More specifically, the disclosed invention can comprise a spectroscopic rotating compensator material system investigation system comprising:

a polarization state generator comprising:
  a source of polychromatic, (ie. broadband), beam of electromagnetic radiation;
  a first aperture with a nominal internal diameter of between 100 and 600 microns;
  a second aperture with a nominal internal diameter has a nominal internal diameter of 3 to 3.5 millimeters;
  a fixed polarizer;
  a rotating compensator;
  a third aperture with a nominal internal diameter of 3.5 millimeters;
  a forth aperture with a nominal internal diameter of 3.75 millimeters;
  a fifth aperture with a nominal internal diameter of 4.8 millimeters;

a stage for supporting a material system;

and a polarization state detector comprising:
  a sixth aperture with a nominal internal diameter of 4.8 millimeters;
  a seventh aperture with a nominal internal diameter of 3.75 millimeters;
  an eighth aperture with a nominal internal diameter of 3.5 millimeters;
  a fixed analyzer;
  a ninth aperture with an adjustable internal diameter;
  an optical fiber; and
  at least one detector system which contains a dispersive element and a multiplicity of detector elements;

there optionally being a UV filter present between said source of a polychromatic beam of electromagnetic radiation and said stage for supporting a material system for the purpose of preventing the effects of UV radiation on a material system.

Further present is said spectroscopic rotating compensator material system investigation system is at least one combined spatial filter and relay system for providing a small spot of electromagnetic radiation on a material system. Said combined spatial filter and relay system can be present between said source of polychromatic, (ie. broadband), beam of electromagnetic radiation and said stage for supporting a material system, and/or between said stage for supporting a material system and said at least one detector system which contains a dispersive element and a multiplicity of detector elements. It is also noted that two combined spatial filter and relay systems can be present between said source of polychromatic, (ie. broadband), beam of electromagnetic radiation and said stage for supporting a material system, and/or between said stage for supporting a material system and said at least one detector system which contains a dispersive element and a multiplicity of detector elements, or one combined spatial filter and relay systems can be present between said source of polychromatic, (ie. broadband), beam of electromagnetic radiation and said stage for supporting a material system, and another present between said stage for supporting a material system, and said at least one detector system which contains a dispersive element and a multiplicity of detector elements.

When said spectroscopic rotating compensator material system investigation system is used to investigate a material system present on said stage for supporting a material system, said fixed analyzer and fixed polarizer are maintained essentially fixed in position and said rotating compensator is caused to continuously rotate while a polychromatic beam of electromagnetic radiation produced by said source of polychromatic beam of electromagnetic radiation is sequentially caused to pass through said first aperture, second aperture, fixed polarizer, rotating compensator, third aperture, forth aperture, first substantally achromatic lens, fifth aperture, said polychromatic beam of electromagnetic radiation also passing through said UV filter, then interact with a material system placed on said stage for supporting a material system, then sequentially pass through said sixth aperture, second substantially achromatic lens, seventh aperture, eighth aperture, fixed analyzer, ninth aperture, enter said optical fiber and therevia enter said detector system.

Preceeding the optical fiber can be a focusing substantially achromatic lens, or an Offner relay, or a present invention combination spatial filter and relay system.

The preferred compensator comprises a selection from the group consisting of:

comprised of a combination of at least two zero-order waveplates, said zero-order waveplates and having their respective fast axes rotated to a position offset from zero or ninety degrees with respect to one another;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates and in said first effective zero-order waveplate;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates and in said first effective zero-order waveplate; and comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate;

and said compensator causes essentially no deviation or displacement in a polychromatic beam of electromagnetic radiation caused to pass therethrough while caused to rotate.

Said compensator provides that retardation effected thereby between orthogonal components of a beam of electromagnetic radiation at one wavelength is different than that provided thereby at at least one other wavelength. Said variation is exemplified as being:

within a range of thirty (30.0) to less than one-hundred-thirty-five (135) degrees over a range of wavelengths defined by a selection from the group consisting of:
  a. minimum wavelength is less than/equal to one-hundred-ninety (190) and maximum wavelength greater than/equal to seventeen-hundred (1700) nanometers;
  b. minimum wavelength is less than/equal to two-hundred-twenty (220) and maximum wavelength MAXW greater than/equal to one-thousand (1000) nanometers;
  c. within a range of wavelengths defined by a maximum wavelength (MAXW) and a minimum wavelength (MINW) range where (MAXW)/(MINW) is at least four-and-one-half (4.5); or being within a range of seventy-five (75.0) to less than one-hundred-thirty-five (135) degrees over a range of wavelengths defined by a selection from the group consisting of:
  a. between one-hundred-ninety (190) and seven-hundred-fifty (750) nanometers;
  b. between two-hundred-forty-five (245) and nine-hundred (900) nanometers;
  c. between three-hundred-eighty (380) and seventeen-hundred (1700) nanometers;
  d. within a range of wavelengths defined by a maximum wavelength (MAXW) and a minimum wavelength (MINW) wherein the ratio of (MAXW)/(MINW) is at least one-and-eight-tenths.

The present invention can utilize essentially any Compensator, some of which are can be selected from the group consisting of:

a single element compensator, (which in the context of the disclosed invention could have its optic axis in the plane of a surface therof, or have its optic axis substantially perpendicular thereto);

a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB)); where the identifiers are shown in FIGS. 9g1-9j.

Additional compensator systems, previously disclosed in patent application Ser. No. 08/997,311, (now U.S. Pat. No. 5,946,098), and CIP's therefrom, which are specifically within the scope of the invention and can be included in the selection group are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation; a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

Continuing, said spectroscopic rotating compensator material system investigation system further comprises, preferably between said fixed polarizer and said ninth aperture, a beam splitting means which serves to divert a portion of the polychromatic beam of electromagnetic radiation which otherwise proceeds to said optical fiber, and transmits the remainder of said polychromatic beam of electromagnetic radiation theretoward, said diverted portion of said polychromatic beam of electromagnetic radiation being directed by said beam splitting means into an alignment means selected from the group consisting of:
  reticule; and
  electromagnetic beam detecting means;

such that in use said alignment means provides monitored alignment capability thereby allowing precise control of the locus of propagation of the portion of said polychromatic beam of electromagnetic radiation which transmits through said beam splitting means. Said electromagnetic beam detecting means can be in functional combination with electronic circuitry means which which serves to automatically align said portion of said polychromatic beam of electromagnetic radiation which is transmitted toward said ninth aperture and optical fiber, based on feedback from said detector.

The prefered detector dispersive optics and detector elements are contained in an off-the-shelf diode array spectrometer system, with an operational wavelength range selected from the group consisting of:
  300-1150 nm;
  190-730 nm;
  190-400 nm; and
  900-2400 nm;

and optionally the detector which demonstrates a quantum efficiency of at least greater than forty (40%) percent.

The dispersive optics is preferably a diffraction grating characterized by a selection from the group consisting of:
  a "lined";
  a "blazed"; and
  a "holographic" geometry;

said lined geometry consisting essentially of symetrical alternating lines with depressions therebetween, and said blazed geometry consisting of alternating ramp shaped lines with depressions therebetween, and said holographic geometry consisting of continuous cosine shaped lines and depressions. However, said dispersive optics can comprise a prism.

While the prefered compensators are described above, functional compensators can be of a type selected from the group consisting of:
  Berek-type with optical axis essentially perependicular to a surface thereof;
  non-Berek-type with an optical axis essentially parallel to a surface thereof;
  zero-order wave plate;
  zero-order waveplate constructed from two multiple order waveplates;
  a sequential plurality of zero-order waveplates, each constructed each from a plurality of multiple order waveplates;
  rhomb;
  polymer;
  achromatic crystal; and
  pseudo-achromatic.

The fiber optic present after said analyzer can be single or at least bifrucated thereby providing a plurality of fiber optic bundles, at least two of which plurality of at least two bifrucated fiber optic bundles provide input to separate detector system), each of said separate detector systems comprising a dispersion optics and a multiplicity of detector elements, said plurality of fiber optic bundles having cross-sectional shapes at ends thereof selected from the group:
  essentially circular;
  essentially slit shaped;
  other than essentially circular; and
  essentially slit shaped.

It is also to be appreciated that the disclosed spectroscopic rotating compensator material system investigation system is characterized by a mathematical model comprising calibration parameters, at least one of which is a member of the group consisting of:
  effective polarizer azimuthal angle orientation ($P_S$);
  present material system PSI ($\psi$), as a function of angle of incidence and a thickness;
  present material system DELTA ($\Delta$), as a function of angle of incidence and a thickness;
  compensator azimuthal angle orientation ($C_S$)
  matrix components of said compensator;
  analyzer azimuthal angle orientation ($A_S$); and
  detector element image persistance ($x_n$) and read-out ($p_n$) nonidealities.

Further, said mathematical model is effectively a transfer function which enables calculation of electromagnetic beam magnitude as a function of wavelength detected by a detector element (DE), given magnitude as a function of wavelength provided by said source of polychromatic beam of electromagnetic radiation (EPCLB). Said calibration parameter(s) selected from the group consisting of:
  effective polarizer azimuthal angle orientation ($P_S$);
  present material system PSI ($\psi$), as a function of angle of incidence and a thickness;
  present material system DELTA ($\Delta$), as a function of angle of incidence and a thickness;
  compensator azimuthal angle orientation;
  matrix components of said compensator ($C_S$) as a function of wavelength;
  analyzer azimuthal angle orientation ($A_S$); and
  detector element image persistance ($x_n$) and read-out ($p_n$) nonidealities;

are, in use, evaluated by performance of a mathematical regression of said mathematical model onto at least one, multi-dimensional, data set(s), said at least one, multi-dimensional, data set(s) being magnitude values vs. wavelength and a at least one parameter selected from the group consisting of:
  angle-of-incidence of said polychromatic beam of electromagnetic radiation with respect to a present material system (MS); and
  effective or actual azimuthal angle rotation of one element selected from the group consisting of:
    said polarizer (P); and
    said analyzer (A);

obtained over time, while said compensator (C) is caused to continuously rotate;

said at least one, multi-dimensional, data set(s) each being normalized to a selection from the group consisting of:
  a data set D.C. component;
  a data set A.C. component;
  a parameter derived from a combinations of a data set D.C. component and a data set A.C. component.

Further, the spectroscopic rotating compensator material system investigation system can be at least partially present in an environmental control chamber characterized by a selection from the group consisting of:

it comprises at least one chamber region in which is present polarization state generator comprising component(s) prior to said material system, said material system, and polarization state detector comprising component(s) after said material system;
  it comprises at least three chamber regions, in one of which is present polarization state generator comprising component(s) prior to said material system, in the second of which is present the material system and in the third of which is present polarization state detector comprising component(s) after said material system;
  it comprises at least two chamber regions, in one of which is present polarization state generator comprising component(s) prior to said material system and said material system, and in the second of which is present polarization state detector comprising component(s) after said material system;
  it comprises at least two chamber regions, in one of which is present polarization state generator comprising component(s) prior to said material system, and in the second of which is present polarization state detector comprising component(s) after said material system and said material system.

It can be beneficial to control atmospheric content, for instance, where UV range wavelengths are utilized as they are absorbed by oxygen and water vapor.

At this point it is beneficial to recite a method of quickly simultaneously taking data at a multiplicity of wavelengths including wavelengths which are, and are not absorbed by environmental components. Said method comprises the steps of:
  a) providing a spectroscopic ellipsometer or polarimeter system comprising a source of a polychromatic beam of electromagnetic radiation, a polarizer, a stage for supporting a material system, an analyzer, a dispersive optics and at least one detector system which comprises a multiplicity of detector elements;

such that when said spectroscopic ellipsometer or polarimeter is used to investigate a material system present on said stage for supporting a material system, a polychromatic beam of electromagnetic radiation produced by said source of a polychromatic beam of electromagnetic radiation is caused to pass through said polarizer and interact with a material system on said stage for supporting a material system, then pass through said analyzer, and interact with said dispersive optics such that a multiplicity of essentially single wavelengths are caused to simultaneously enter a corresponding multiplicity of detector elements in said at least one detector system;

said spectroscopic ellipsometer or polarimeter system further comprising an environmental control chamber in which the spectroscopic ellipsometer or polarimeter is contained, said environmental control chamber being characterized by a selection from the group consisting of:
  it comprises at least one chamber region in which is present polarization state generator comprising component(s) prior to said material system, said material system, and polarization state detector comprising component(s) after said material system;
  it comprises at least three chamber regions, in one of which is present polarization state generator comprising component(s) prior to said material system, in the second of which is present the material system and in the third of which is present polarization state detector comprising component(s) after said material system;

it comprises at least two chamber regions, in one of which is present polarization state generator comprising component(s) prior to said material system and said material system, and in the second of which is present polarization state detector comprising component(s) after said material system;

it comprises at least two chamber regions, in one of which is present polarization state generator comprising component(s) prior to said material system, and in the second of which is present polarization state detector comprising component(s) after said material system and said material system.

b) placing a material system on said stage for supporting a material system and at least partially purging or evacuating said environmental control chamber;

c) causing said source of polychromatic beam of electromagnetic radiation to provide a polychromatic beam of electromagnetic radiation and causing said beam to interact with said material system on said stage for supporting a material system, and interact with said dispersive optics such that a multiplicity of essentially single wavelengths are caused to simultaneously enter a corresponding multiplicity of detector elements in said at least one detector system.

Said method of quickly simultaneously taking data at a multiplicity of wavelengths can involve providing at least one detector system which comprises a multiplicity of detector elements involves providing a one-dimensional array or a multi-dimensional array.

Further, it is generally known that many sources of electromagnetic radiation which provide wavelengths down to and below 193 nm typically provide said wavelengths at a lower intensity than is associated with longer wavelengths. Also, it is known that optical elements through which electromagnetic radiation is caused to pass often have different effects on different wavelengths, with a result being that electromagnetic radiation of one wavelength proceeds along a different path than does electromagnetic radiation of a different wavelength. Where said electromagnetic radiation is to be focused onto a spot on a material system said dispersion can lead to the spot being of a diameter greater than 35 micron. Disclosed in this Specification are a number of approaches to improving intensity at short wavelengths and of reducing spot size of electromagnetic radiation where it is caused to impinge upon a material system surface.

A first approach is to provide a back reflector behind a source of electromagnetic radiation, which serves to direct electromagnetic radiation which exits the source in a useful direction.

Another approach is to provide a reflecting means in the pathway of the electromagnetic beam, upon which reflecting means is a coating which emphasises reflection of the UV and particularly at 193 nm. An example of such a coating on a reflective means is 600 Angstroms of Silicon Dioxide atop Silicon. This approach enables setting "gain" providing means at higher levels to emphasize UV signals, while not over amplifying, and even saturating higher intensity wavelengths signals.

Another approach is to coat transmissive elements such as lenses present in the system, to minimize entry and exit losses caused thereby, and improve overall UV transmission therethrough. An example is a single 300 Angstrom layer of $MgF_2$. Multilayer coatings can also be used.

Another approach is to provide a Grating which has characteristics that emphasize UV wavelengths and/or direct a utilized "Order" of wavelengths in a direction which is subject to less influence by the zero and/or other orders.

Further, application of baffling to block access of zero and/or other orders of electromagnetic radiation to detector means can be applied.

Approaches which focus on optical fibers are:

Another approach is to eliminate optical fibers which, while convenient for use directing electromagnetic radiation, also serve to attenuate UV wavelength intensity via entry loss and transmission attenuation.

However, if optical fibers are utilized, to reduce UV intensity at fiber entry loss a narrow slit (eg. smaller that the fiber dimension), can be placed at the entry to the fiber.

The following approaches focus on increasing the amount of UV electromagnetic radiation and can be practiced independently or in combination:

Another approach is to utilize a source of electromagnetic radiation which emphasises UV wavelength production. Various wattage lamps (eg. 35, 75 and 150 can be applied and where necessary can involve application of various indirect heat sink based cooling and produced ozone containment.

Another approach is to, in the case of rotating compensator ellipsometers, reduce the rotation speed of the compensator so that for the same number of rotations more total electromagnetic radiation passes therethrough and reaches the detector.

Another approach is to take multiple scans of data to improve signal to noise.

Another approach is to combine the output of multiple pixels in a detector which receive UV radiation.

An approach which is focused on providing a small spot size, (eg. 35 mm), is to identify optical elements which enter dispersion of wavelengths entered thereinto and reduce their effect. Dispersion, it should be appreciated causes different wavelengths in electromagnetic radiation to focus at different points on a material system. Reduced dispersion can be accomplished by, for instance, adding optical elements which offset the effect entered by existing optical elements. While increasing physical dimensions and potentially adding entry and exit and transmission attenuation effects, the result can be a smaller spot size.

In ellipsometry applications, for instance, said system further comprises a polarizer in the pathway of said collimated beam of electromagnetic radiation, which polarizer can be selected from the group consisting of:
Calcite;
BBO;
MgFl;

to impose a state of substantially linear polarization thereupon in wavelength ranges 1100 nm and about:
245 nm;
220 nm; and
193 nm;

respectively.

The disclosed invention will be better understood by reference to the Detailed Disclosure Section of this Specification, in combination with the Drawings.

SUMMARY OF THE INVENTION

It is a primary purpose and/or objective of disclosed invention to teach application of combined spatial filter and reflective relay systems in rotating compensator ellipsometer, polarimeter and the like systems.

It is another purpose and/or objective of disclosed invention to teach application of 1:1 reflective relay systems as taught in expired U.S. Pat. No. 3,748,015, in rotating compensator ellipsometer, polarimeter and the like systems.

Other purposes and/or objectives of disclosed invention will become apparent upon a reading of the Specification and Claims.

BRIEF DESCRIPTION OF THE DRAWINGS

FIGS. 6a and 6b demonstrate how a Circular Beam (in cross-section), appears when impinged onto the Surface of a Sample at an oblique Angle-of-Incidence.

FIGS. 6c and 6d demonstrate non-circular Apertures which offset the effect shown in FIG. 6b.

FIG. 9a shows a Fiber Optic which is essentially circular at the left side and which becomes of a "slit" shape at the right side.

FIG. 9b shows a Fiber Optic which is essentially circular shaped along the entire length thereof, and which provides input to a "Slit" per se.

FIG. 9c shows a Trifrucated Fiber Optic which is essentially circular at the left side, which trifrucates and then is exemplified as becoming circular or of a "slit" shape at the right side.

FIG. 9d shows a Berek-type Compensator with an Optical Axis perpendicular to a surface thereof.

FIG. 9e shows a Compensator with an Optical Axis parallel to a surface thereof.

FIG. 9f demonstrates construction of a Zero-Order Quartz Waveplate from two Multiple Order waveplates.

FIGS. 9g1, 9h and 9i demonstrate construction of a preferred compensator system constructed from first and second effective Zero-Order Waveplates, each of which effective Zero-Order Waveplates is a constructed composite of two Multiple Order waveplates, the fast axes of which at least two composite effective Zero-Order Waveplates are oriented away from zero or ninety degrees, and at a nominal forty-five degrees, with respect to one another. Optional additional third element(s) are indicated by dashed lines.

FIG. 9g2 shows three Zero Order Plates are contacted to one another instead of having space thereinbetween. Three element Compensators configured as suggested by FIGS. 9g1, 9g2 and 9j can comprise a "Psuedo Achromatic" which can provide FIG. 9j demonstrates functional construction of another preferred compensator system constructed from first and second actual per se. Zero-Order Waveplates, each of which actual per se. Zero-Order Waveplate is an effective single plate, the fast axes of which at least two composite actual per se. Zero-Order Waveplates are oriented away from zero or ninety degrees, and at a nominal forty-five degrees, with respect to one another.

FIGS. 9k1-9q demonstrate additional compensators which can be applied in the present invention.

DETAILED DESCRIPTION

It is to be appreciated that the distinguishing aspect of the present of the present invention is the presence of at least one combined spatial filter and relay system in the context rotating compensator ellipsometer, polarimeter or the like system as Claimed in Parent U.S. Pat. No. 5,872,630to Johs. Hence, the presentation in the Section of the Specification begins with a detailed disclosure of a background "Offner" relay system, and modified versions thereof as applied in the present invention.

Figure 1:
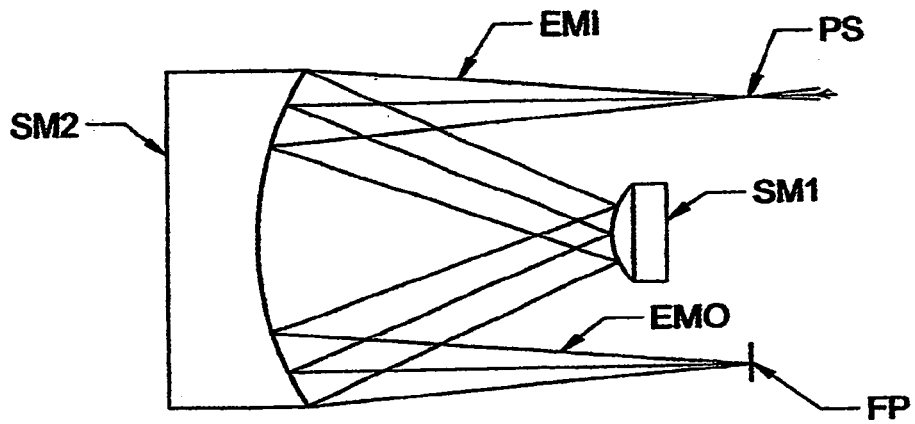
FIG. 1 shows a prior art 1:1 relay system.

Turning now to FIG. 1, there is shown a system disclosed in expired U.S. Pat. No. 3,748,015 to Offner. Indicated is a relay system comprising two elements:
 a) a concave spherical mirror (SM2); and
 c) a convex spherical mirror (SM1).

Said elements (SM2) and (SM1) are arrange such that electromagnetic radiation (EM1) caused to approach the concave spherical mirror (SM2) reflects at a first location thereon, and is reflected to said a convex spherical mirror (SM1), from which it reflects onto a second location of said concave spherical mirror (SM2), from which it reflects as a beam of electromagnetic radiation (EMO) with an image point (FP), if the electromagnetic radiation (EMI) which is caused to approach the concave spherical mirror (SM2) at a first location thereon was, for instance, an equivalent to a point source (PS). The 015 patent describes the focal length of the concave spherical mirror (SM2) and being twice the focal length of the convex spherical mirror (SM1).

Figure 2A:
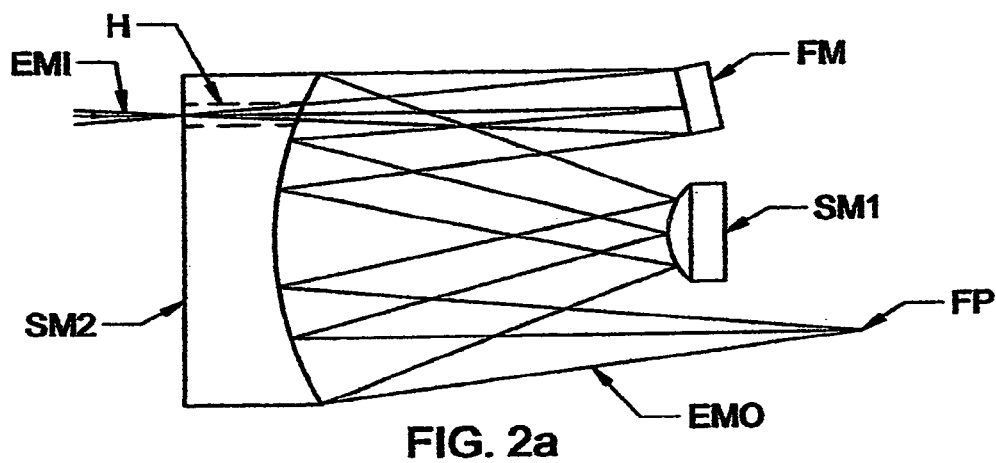
FIG. 2a shows a first embodiment of a combined present invention spatial filter and relay system.

FIG. 2a shows a combined spatial filter and relay system comprising three elements:
 a) a concave spherical mirror (SM2) having at least one concave spherical surface and an aperture hole (H) therethrough;
 b) a flat mirror (FM); and
 c) a convex spherical mirror (SM1) having at least one convex spherical surface.

Said elements are arranged such that electromagnetic radiation (EM1) caused to approach the concave spherical mirror (SM2) passes through said aperture hole (H) and reflects from said flat mirror (FM) onto a first location of a concave surface of said concave spherical mirror (SM2), then reflects from said first location onto a convex spherical surface of said convex spherical mirror (SM1) and reflects therefrom onto a second location of said concave surface of said concave spherical mirror (SM2) as a converging beam of electromagnetic radiation. Note that the electromagnetic radiation approaches the Concave Mirror (SM2) from "back" side thereof. Said "back" side can be of any functional shape, but is shown as being flat for demonstrative purposes.

Figure 2B:
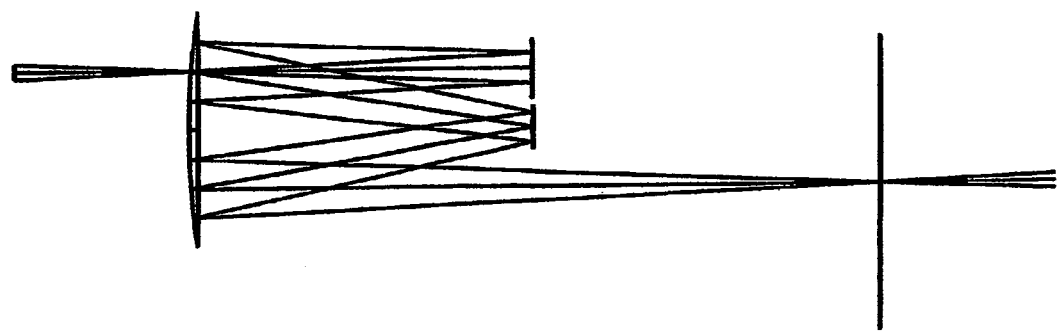
FIGS. 2b-2e show ray traces of how the FIGS. 1 and 2a system effects beams with various characteristics.
Figure 2C:
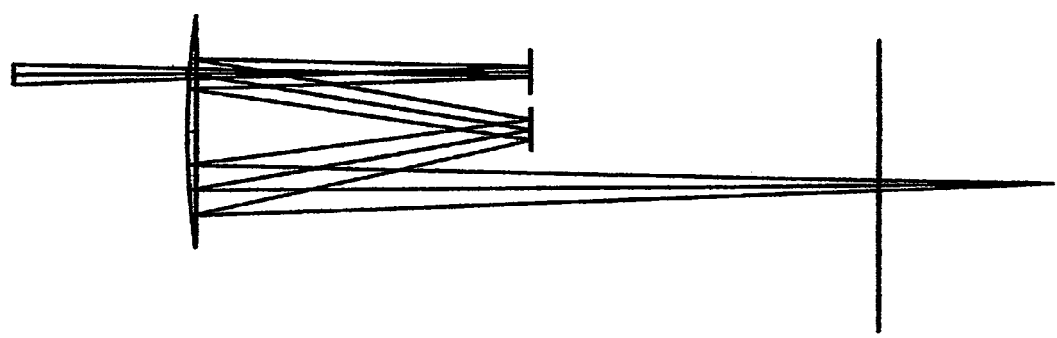
Figure 2D:
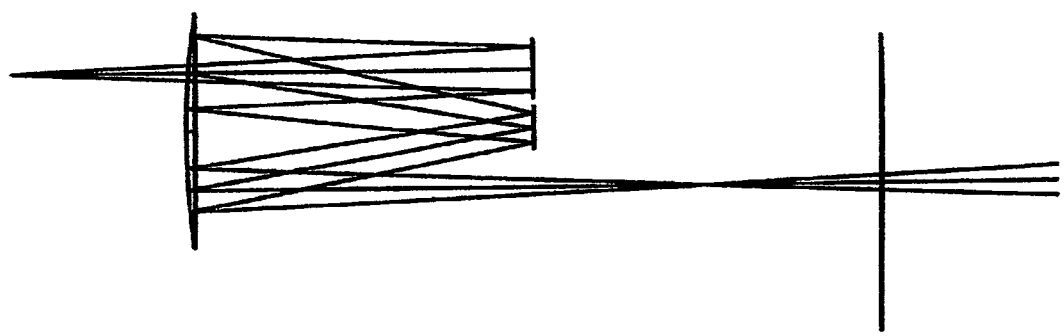
Figure 2E:
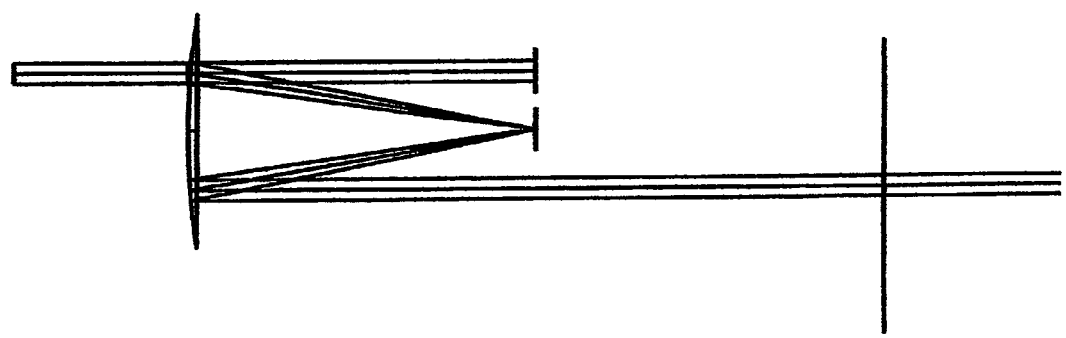

For insight, FIGS. 2b-2e show ray traces of how the FIG. 2a system effects beams with various characteristics. FIG. 2b shows a rays equivalent to those in FIG. 2a. FIGS. 2c and 2d show an effective point source of a beam need not be at the Spatial Filter (H), and FIG. 2e demonstrates the use of a collimated beam in a FIG. 1 system, and the relay characteristic of the system.

Figure 3:
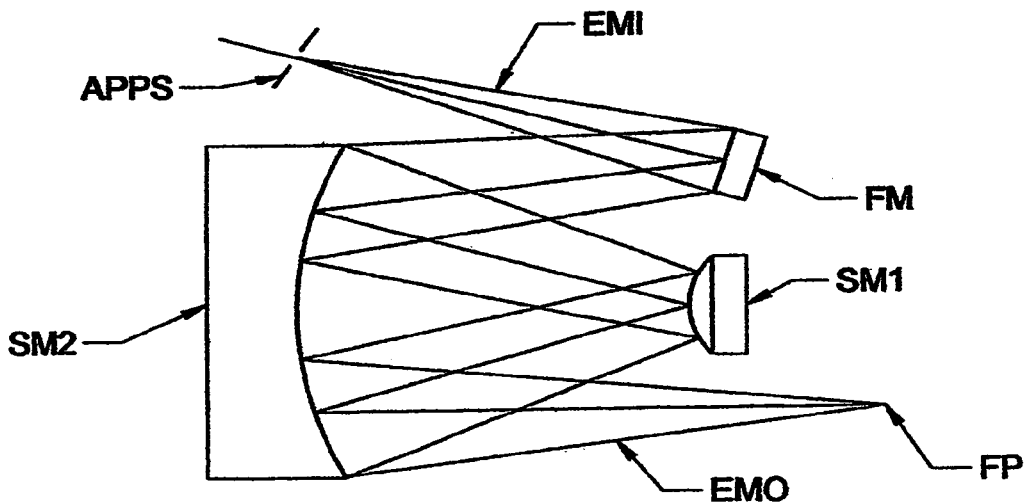
FIG. 3 shows a second embodiment of a combined present invention spatial filter and relay system.

FIG. 3 shows a present invention combined spatial filter and relay system comprising:
 a) an aperture (APPS);
 b) a flat mirror (FM);
 c) a concave spherical mirror (SM2) having at least one concave spherical surface; and
 d) a convex spherical mirror (SM1) having at least one convex spherical surface.

Said elements are arranged such that electromagnetic radiation (EMI) from said aperture (H) is caused to approach the flat mirror (FM) and reflect therefrom onto a first location of a concave surface of said concave spherical mirror (SM2), reflect from said first location onto a convex spherical surface of said convex spherical mirror (SM1) and reflect therefrom onto a second location of said concave surface of said concave spherical mirror (SM2) from which it reflects as a converging beam of electromagnetic radiation with an image point (FP). It is assumed in this embodiment that an effective point Source (PS) is present as a source of the beam of electromagnetic radiation (EMI).

Figure 4:
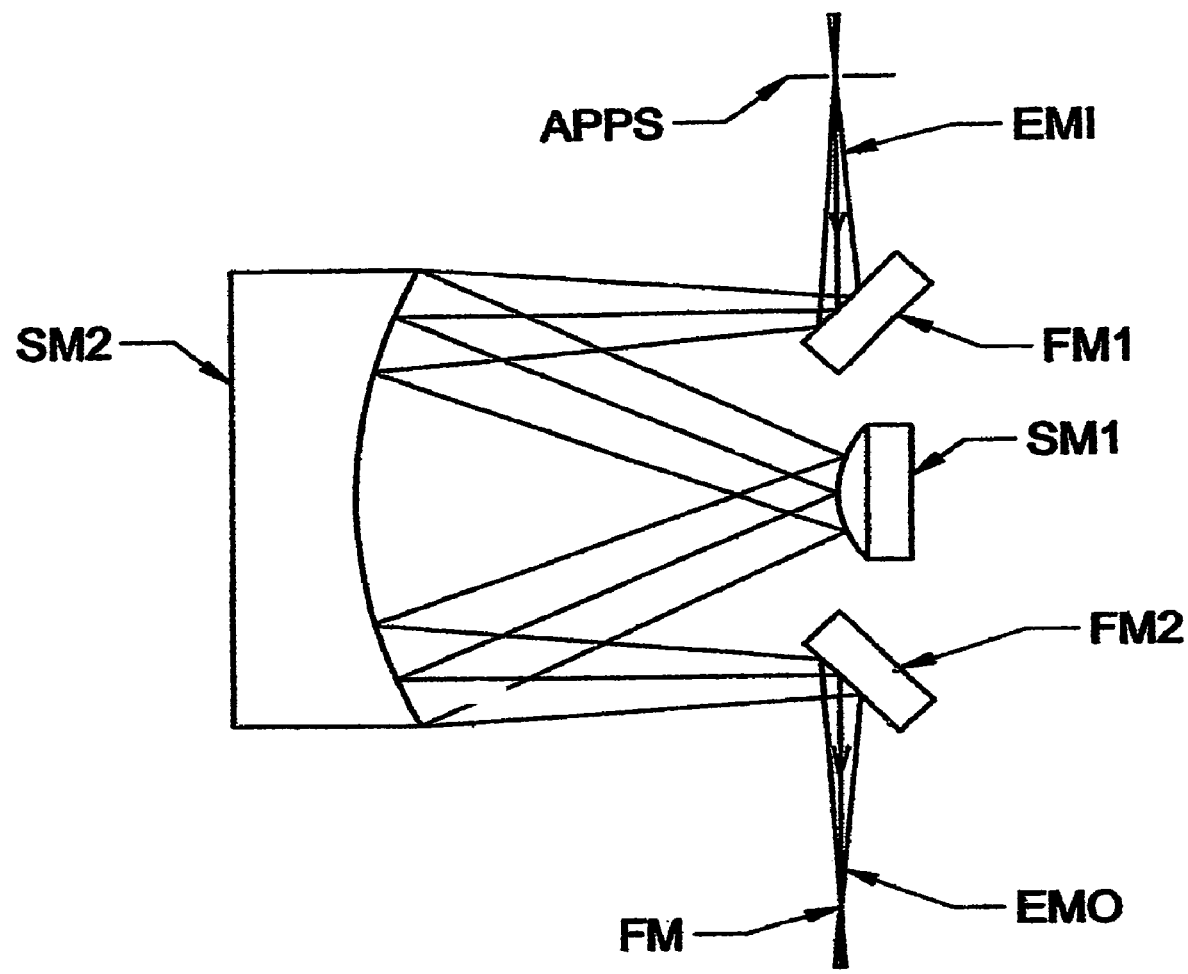
FIG. 4 shows a third embodiment of a combined present invention spatial filter and relay system.

FIG. 4 shows a combined spatial filter and relay system comprising five elements:
 a) an aperture (APPS);
 b) a first flat mirror (FM1);
 c) a concave spherical mirror (SM2) having at least one concave spherical surface;
 d) a convex spherical mirror (SM1) having at least one convex spherical surface; and
 e) a second flat mirror (FM2).

Said elements are arranged such that electromagnetic radiation (EM1) from said aperture (APPS) is caused to approach the first flat mirror (FM1) and reflect therefrom onto a first location of a concave surface of said concave spherical mirror (SM2), reflect from said first location onto a convex spherical surface of said convex spherical mirror (SM1) and reflect therefrom onto a second location of said concave surface of said concave spherical mirror (SM2) from which it reflects onto said second flat mirror (FM2) which is positioned to intercept and reflect electromagnetic radiation reflected from said second location of said concave surface of said concave spherical mirror (SM1), as a converging beam of electromagnetic radiation (EMO) with an image point (FP). Note that the electromagnetic radiation approaches and reflects from both first flat mirror (FM1), and said second flat mirror (FM2), at 45 degree angles.

(It is noted that while said first (FM1) and second (FM2) flat mirrors are typically oriented so that a beam of electromagnetic radiation approaches along a 45 degree Angle-of-Incidence, the present invention is not limited to such a configuration. That is, said Angles-of-Incidence can be any functional angle, where, for instance, compensating adjustments are made in FIGS. 5a and 5b to effect an intended Angle-of-Incidence of the beam of electromagnetic radiation where it impinges on a Surface of said Sample (SS), and/or reflects therefrom.

Figure 5A:
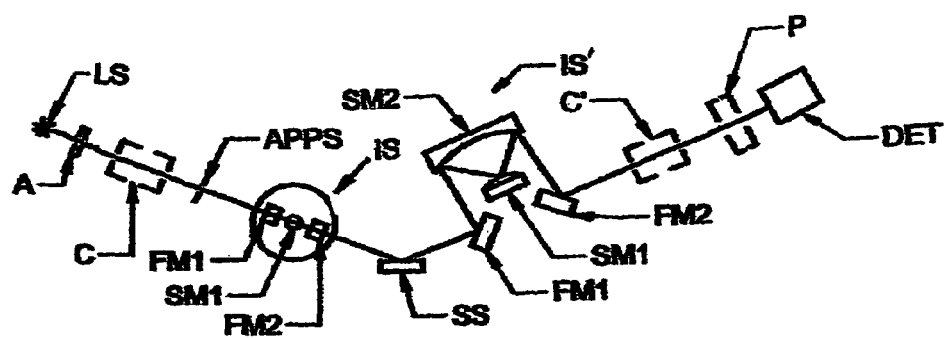
FIG. 5a show that two relay systems as shown in FIG. 4, which are rotated 90 degrees with respect to one another, can be oriented, one on the input, and one on the output side of a material system, to minimize their effect on a beam of electromagnetic radiation caused to pass therethrough.

FIG. 5a shows a present system for investigating a material system comprising:
 a source of electromagnetic radiation (LS);
 an aperture;
 first (IS) and second (IS') relay systems, each thereof comprising four elements, as shown in FIG. 4 to be:
   a) a first flat mirror (FM1);
   b) a concave spherical mirror (SM2) having at least one concave spherical surface;
   c) a convex spherical mirror (SM1) having at least one convex spherical surface; and
   d) a second flat mirror (FM2);

said elements being arranged as described with respect to FIG. 4;

and a detector (DET);

said Sample (SS) being positioned between said first and second relay systems.

Said first (IS) relay system is positioned to relay electromagnetic radiation (EMI) from the source (LS) thereof as it passes through said aperture (APPS), and direct it onto a surface of said Sample (SS) at an oblique angle of incidence, and said second (IS') relay system is positioned to receive electromagnetic radiation reflected from the Sample (SS) and pass it on to said detector (DET);

the propagation direction of electromagnetic radiation entering and exiting each of said first (IS) and second (IS') relay systems being substantially unchanged by passing therethrough;

said system being further characterized in that a plane formed by the locus of the electromagnetic radiation passing through the first (IS) relay system is oriented 90 degrees to a plane formed by the locus of the electromagnetic radiation passing through the second (IS') relay system, the purpose being to minimize effects of said first (IS) and second (IS') relay systems on a polarization state of said electromagnetic radiation which passes through both thereof.

Figure 5B:
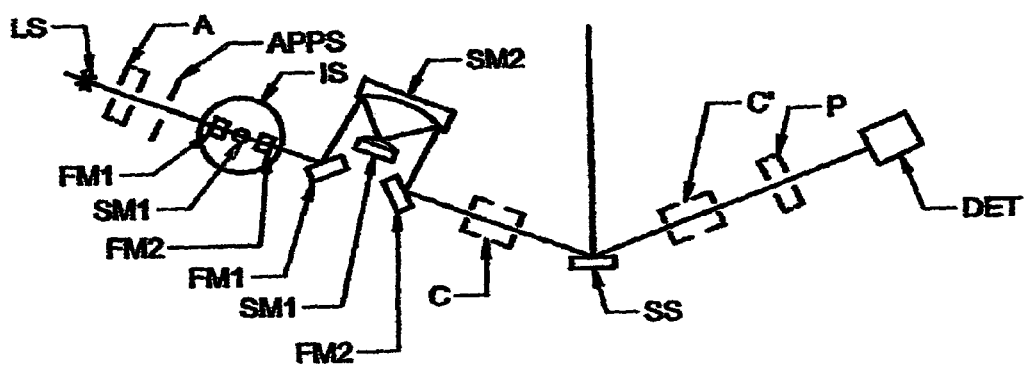
FIG. 5b shows that two relay systems as shown in FIG. 4, which are rotated 90 degrees with respect to one another, can be oriented, both on the input, (or output) side of a material system, to minimize their effect on a beam of electromagnetic radiation caused to pass therethrough.

FIG. 5b shows a variation of the FIG. 5a system for investigating a material system and comprises:
 a source of electromagnetic radiation (LS);
 an aperture (APPS);
 first (IS) and second (IS') relay systems, each thereof comprising four elements:
   a) a first flat mirror (FM1);
   b) a concave spherical mirror (SM2) having at least one concave spherical surface;
   c) a convex spherical mirror (SM1) having at least one convex spherical surface; and
   d) a second flat mirror (FM2);

and a detector. Again, both the first (IS) and second (IS') relay systems are arranged as shown in FIG. 4. Note, however, that said first (IS) and second (IS') relay systems are both positioned on the same side of the Sample (SS), as opposed what is shown in FIG. 5a. (Note, while not specifically shown, it is to be understood that both the first (IS) and second (IS') relay systems could be present after said Sample (SS)).

It is to be noted that in both FIGS. 5a and 5b, the relay systems (IS) and (IS') are oriented with respect to one another such that a plane formed by the locus of the electromagnetic radiation passing through the first (IS) relay system is oriented 90 degrees to a plane formed by the locus of the electromagnetic radiation passing through the second relay (IS') system. The purpose is to minimize effects of said first (IS) and second (IS') relay systems on a polarization state of said electromagnetic radiation which passes through both thereof.

FIGS. 5a and 5b can be modified to provide a present system for investigating a material system can also comprising:
- a source of electromagnetic radiation (LS);
- an aperture (APPS);
- a combined spatial filter and relay system comprising three elements:
  a) a concave spherical mirror (SM2) having at least one concave spherical surface and an aperture hole (H) therethrough;
  b) a flat mirror (FM); and
  c) a convex spherical mirror (SM1) having at least one convex spherical surface;

and a detector (DET).

FIGS. 5a and 5b can also be modified to provide a present system for investigating a material system comprising:
- a source of electromagnetic radiation (LS);
- an aperture (APPS);
- present invention combined spatial filter and relay system comprising:
  a) an aperture (APPS);
  b) a flat mirror (FM);
  c) a concave spherical mirror (SM2) having at least one concave spherical surface; and
  d) a convex spherical mirror (SM1) having at least one convex spherical surface;

and a detector (DET).

By reference to FIGS. 5a and 5b, it should be apparent that a second combined spatial filter and relay system could be present in a functional position and orientation. However, as the electromagnetic beam (EMI) approaches the flat mirror-(FM) thereof at a more normal angle-of-incidence, it is less necessary to correct for the different effects on "P" and "S" components of said (EMI).

It is noted that in the FIGS. 5a and 5b configurations, an optional Polarizer (P) can be placed between said Source (LS) and Sample (SS); and an optional Analyzer (A) between said Sample (SS) and Detector (DET) to form an ellipsometer system, and at least one Compensators(s) (C) (C') can be placed between the Polarizer (P) and Analyzer (A) to provide a Polarimeter system. Where the Polarizer (P), Compensator (C) (C') and Analyzer (A) are present the system can be operated as a rotating compensator ellipsometer system. FIGS. 5a and 5b demonstrate that the Compensator (C) can be placed before or after a Relay System (IS).

Further, in all embodiments, it is to be understood that the Spatial filter Aperture (H) or (APPS) can be of a typical Circular, or of another shape. For instance, the Aperture (H) or (APPS) can be elliptical and oriented so that a beam of electromagnetic radiation passing therethrough is elongated laterally, so that as the beam impinges on the Surface of said Sample (SS) at an oblique angle, (see FIGS. 5a and 5b), which produced a longitudinally elongated result on the Surface of said Sample (SS), it defines a circular spot thereupon. FIGS. 6a and 6b demonstrate how a Circular Beam (in cross-section), appears when impinged onto the Surface of a Sample (SS) at an oblique Angle-of-Incidence. If, however, the Beam is passed through an Aperture which is not Circular, (see FIG. 6c which shows an Aperture with major and Minor Radii, (rw) and (rl), it will appear as Circular when it is impinged onto the Surface of a Sample (SS) at an oblique Angle-of-Incidence. FIG. 6d shows that a similar effect is achieved by rotating a Circular Aperture (H) or (APPS) so that a beam of electromagnetic radiation does not approach it along a perpendicular locus to a plane formed by the plate in which the Aperture (H) is present. FIGS. 6c and 6d demonstrate actually non-circular aperture and effectively non-circular aperture approaches, respectively, to making a Beam of electromagnetism non-circular prior to impinging onto the Surface of Sample (SS) at an oblique angle, so that said impinging Beam is elongated laterally. When the longitudinal lengthening then occurs, the result is a Circular Spot on the Surface of the Sample.

Figure 7A:
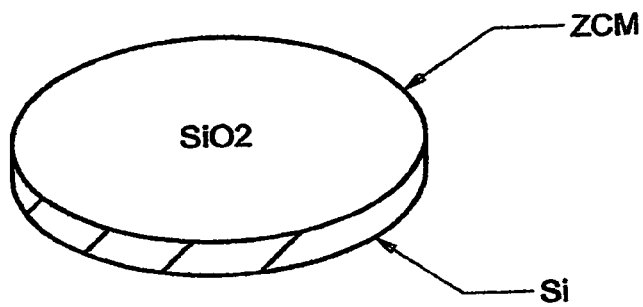
FIGS. 7a and 7b show a silicon substrate with a layer of SiO2 on a top surface thereof, and said silicon substrate with incident and reflected electromagnetic beams.
Figure 7B:
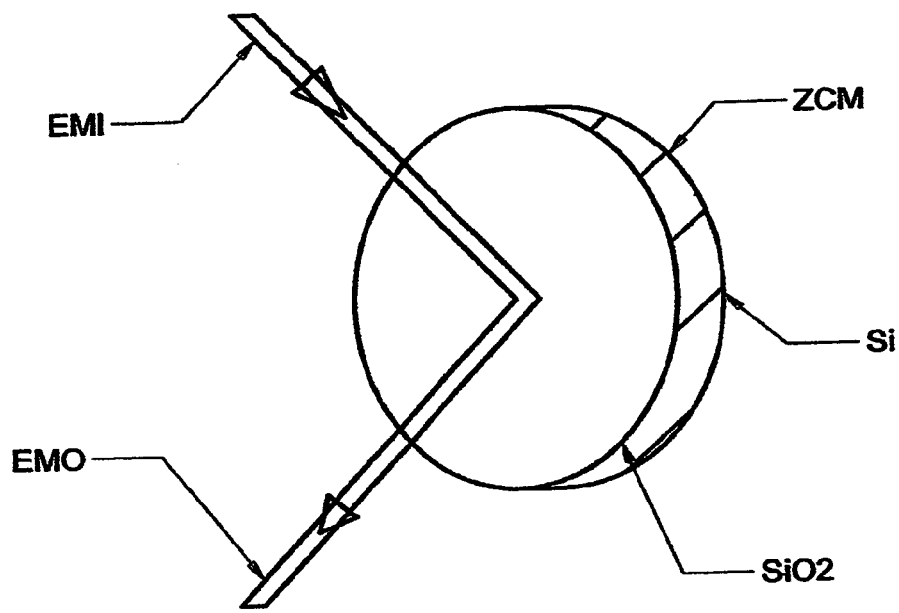
Figure 7C:
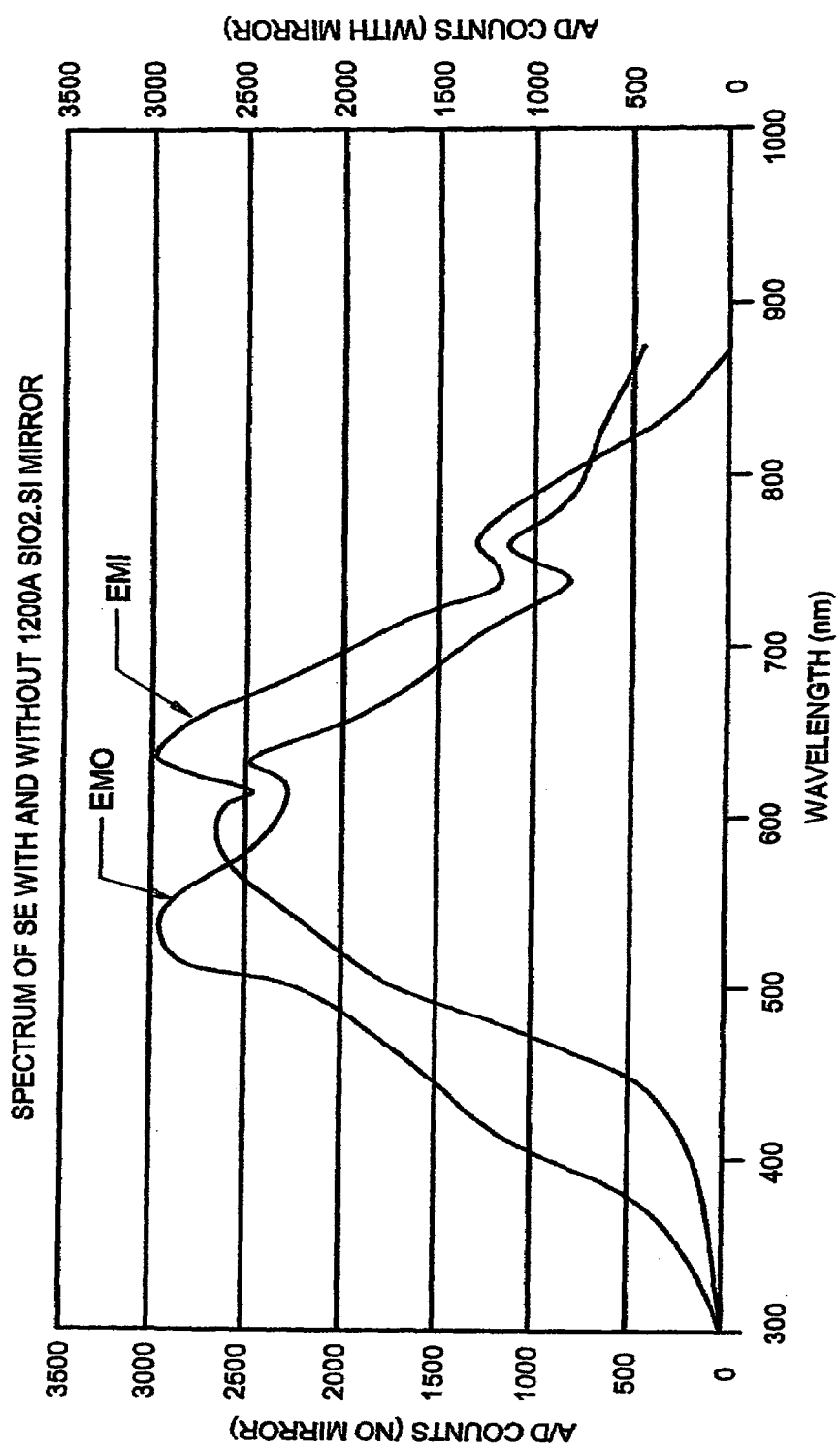
FIG. 7c demonstrates how the system of FIGS. 7a and 7b affect the relative Intensity vs. Wavelength plots of the incident and reflected beams.

It is also noted that any of the reflective surfaces, (eg. Reflective Surfaces of (FM) (when present), (SM1), (SM2) and (FM2) (when present), can be coated with a thin layer of material which alters the Energy vs. Wavelength Spectrum of the beam of electromagnetic radiation which reflects therefrom. For instance, a thin layer of SiO2 has been found to increase relative Intensity of reflected electromagnetic radiation in the IR and UV ranges, as compared to that of wavelengths in the Visible range. As a specific example of the effect a reflective surface can have on the Intensity vs. Wavelength plot of a reflected beam of electromagnetic radiation, FIGS. 7a and 7b are included to show a silicon substrate with a layer of SiO2 on a top surface thereof, and said silicon substrate with incident and reflected electromagnetic beams. FIG. 7c demonstrates how the system of FIGS. 7a and 7b affects the relative Intensity vs. Wavelength plots of the incident and reflected beams.

It is noted that the preferred relay system provides a 1:1 relationship between what is input thereto and what is output therefrom. Specifically, the preferred reflective optics in the present invention which provide electromagnetic radiation onto a material system, are not magnifying or focusing, but rather relay an effective point source of electromagnetic radiation which is, preferably an aperture which functions as a spatial filter. Said relay optics per se. are taught in an expired patent.

Figure 8:
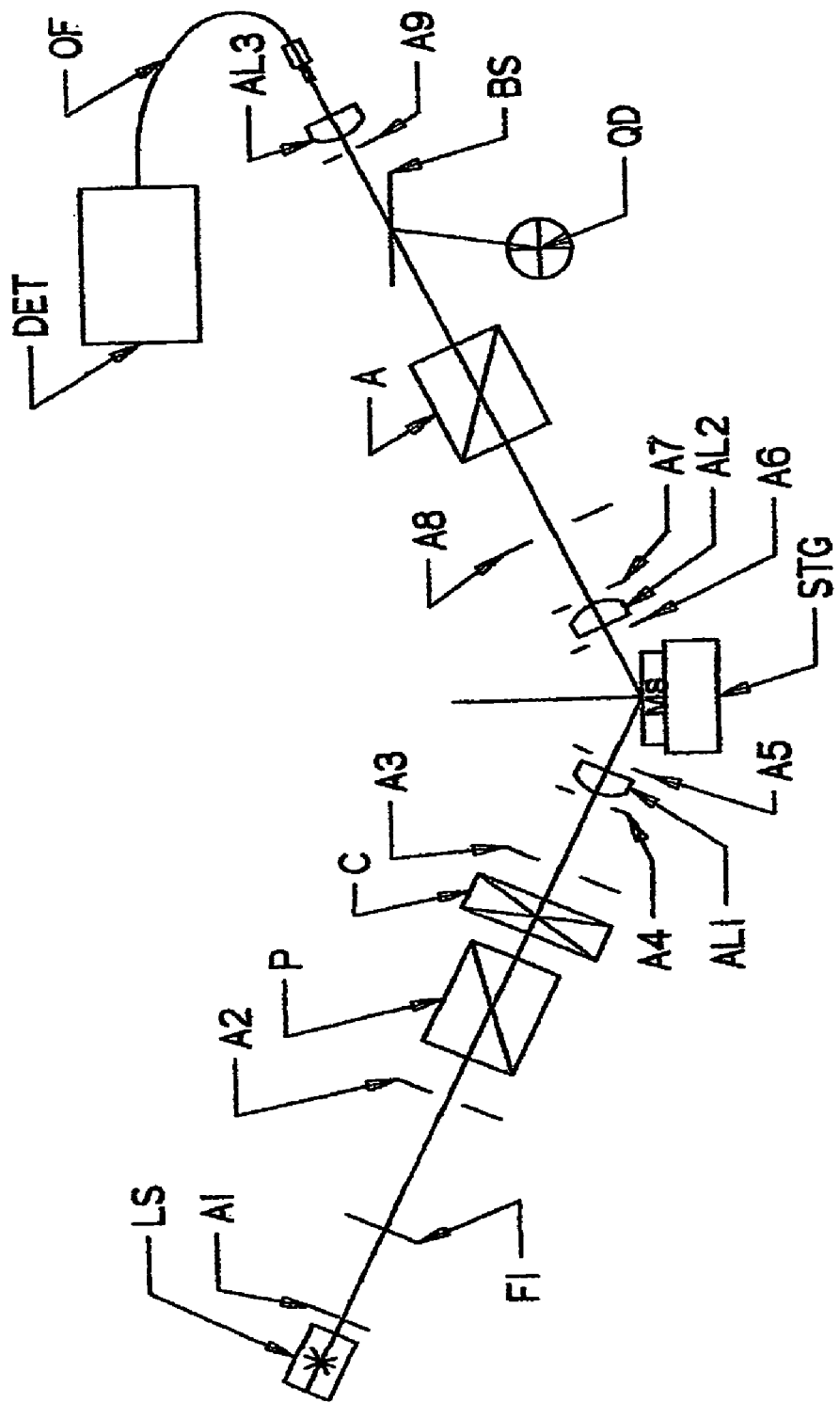
FIG. 8 shows the components of a Refractive based focusing Reflectance Mode Material System Investigation Systems which has five apertures in the pathway of an electromagnetic beam prior to a material system, and four thereafter.

For insight, FIG. 8 shows a spectroscopic rotating compensator material system investigation system comprising refractive focusing. Shown are a source (LS) of polychromatic beam of electromagnetic radiation, a first aperture (A1), a second aperture (A2), a fixed polarizer (P), a rotating compensator (C), a third aperture (A3), a forth aperture (A4), a first substantally achromatic lens (AL1), a fifth aperture (A5), a stage (STG) for supporting a material system, a sixth aperture (A6), a second substantially achromatic lens (AL2), a seventh aperture (A7), an eighth aperture (A8), a fixed analyzer (A), a ninth aperture (A9), a third substantially achromatic lens (AL3), an optical fiber (OF) and a detector system (DET) which contains a dispersive element and a multiplicity of detector elements, there further being a UV filter (F1) present between said source (LS) of polychromatic beam of electromagnetic radiation and said stage (STG) for supporting a material system. When said spectroscopic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantally achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantally achromatic lens (AL2), seventh aperture (A7), eighth aperture (A8), fixed analyzer (A), ninth aperture (A9), third substantially achromatic lens (AL3), enter said optical fiber (OF) and therevia enter said detector system (DET). The present invention system removes at least one of said first (AL1) and second (AL2) substantally achromatic lenses and replaces it with a combined spatial filter and relay system as described above and shown in FIGS. 1-4.

It is also noted that a Compensator Means (C) (C') can utilize an Off-the-Shelf Quarter-Wave-Plate with its Optical Axis in the plane of a surface thereof, (see FIG. 9e), and that a Pseudo-Zero-Order Waveplate can be constructed from two (2) Multiple-Order Waveplates of different thicknesses (T1) and (T2) which have Optical Axes oriented Ninety (90) degrees to one another, such that the overall effect of retardation is in the Zero-Order, (see FIG. 9f). As discussed in more detail below, FIGS. 9g1-9j show that a particularly relevant Compensator Means involves a combination of two compensators means, each selected from the group consisting of: (actual or pseudo Quarter-Wave-Plates). Also, a Berek-type Compensator with its Optical Axis perpendicular to a surface thereof, (see FIG. 9d), can be is selected without special concern to its Achromatic Operating Characteristics, emphasis added. As well, said Compensator Means (C) (C') can be made of essentially any functional material such as Quartz or Polymer etc.

FIGS. 9a-9e are included to indicate tht opticl fibers can be applied in the present invention system. FIG. 9a shows a Fiber Optic which is essentially circular at the left side and which becomes of a "slit" shape at the right side. FIG. 9b shows a Fiber Optic which is essentially circular shaped along the entire length thereof, and which provides input to a "Slit" per se. FIG. 9c shows a Trifrucated Fiber Optic which is essentially circular at the left side, which trifrucates and then is exemplified as becoming circular or of a "slit" shape at the right side. FIG. 9d shows a Berek-type Compensator with an Optical Axis perpendicular to a surface thereof. FIG. 9e shows a Compensator with an Optical Axis parallel to a surface thereof. FIG. 9f demonstrates construction of a Zero-Order Quartz Waveplate from two Multiple Order waveplates.

Figure 9H:
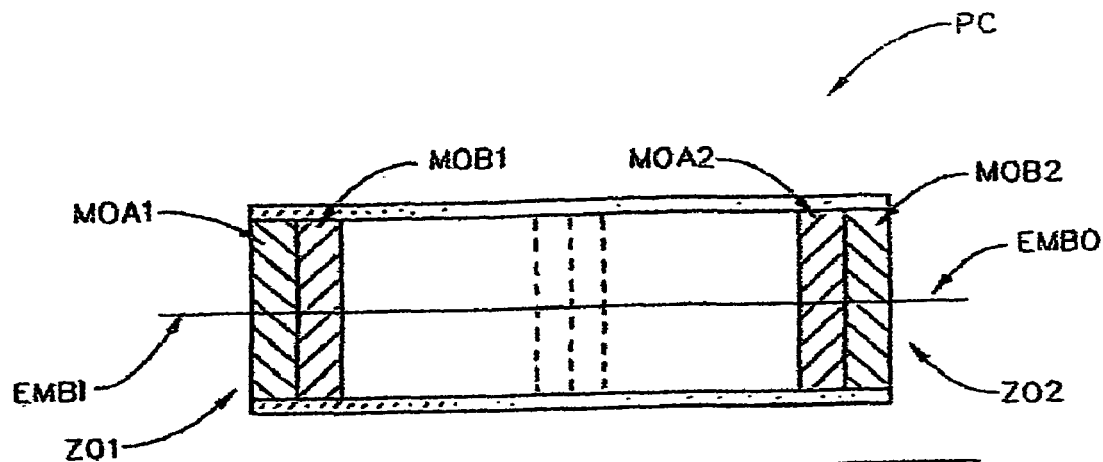
Figure 9H:
Figure 9H:
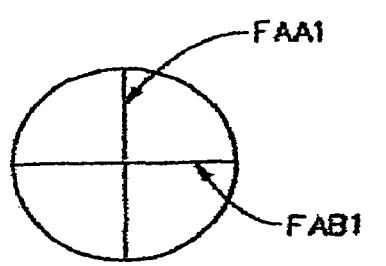
Figure 9I:
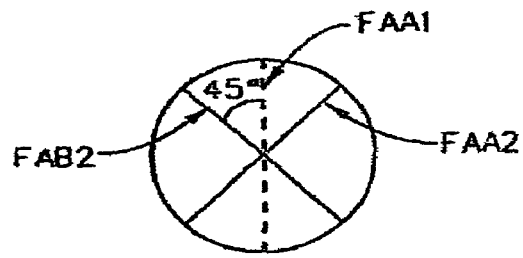
Figure 9J:
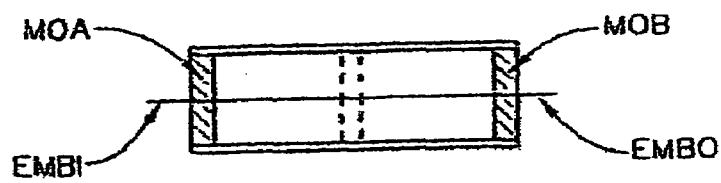

FIGS. 9g1, 9h and 9i demonstrate functional construction of a preferred compensator means system constructed from first (ZO1) and second (ZO2) effectively Zero-Order, (eg. Quartz or Bicrystaline Cadmium Sulfide or Bicrystaline Cadmium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 9g1 is a cross-sectional side view of a preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof vs. Wavelength. FIGS. 9h and 9i are views looking into the left and right ends of the preferred Compensator Means (PC) as shown in FIG. 9g1, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1). (Note that the fast axis (FAA1) of the first effective Zero-Order Waveplate (ZO1) is shown as a dashed line in FIG. 9i, for reference). FIG. 9j demonstrates functional construction of another preferred compensator which is constructed from two per se. single plate Zero-Order Waveplates (MOA) and (MOB), which are typically made of materials such as mica or polymer. Note, It is to be understood that the space between retarder plates in FIGS. 9g1 and 9j can be reduced from that shown, even to the point where said retarder plates make contact with one another. Hence the presence of the spatial separation of the retarder plates shown in FIGS. 9g1 and 9j is not to be interpreted as indicating a required limitation. FIG. 9g2 shows three Zero Order Plates are contacted to one another instead of having space thereinbetween. Three element Compensators configured as suggested by FIGS. 9g1, 9g2 and 9j can comprise a "Psuedo Achromatic" which can provide non-constant Retardation vs. Wavelength characteristics. Note that FIGS. 9g1 and 9j show optional third elements present as dashed-lines. Addition of elements allows achieving a Compensator that provides better Psuedo-Achromatic characteristics than does a single or dual element Compensator.

It is specifically to be understood that a compensator means system can be comprised of at least one Zero-Order waveplate and at least one effectively Zero-Order waveplate in combination, as well as combinations comprised of two actual Zero-Order waveplates or two effectively Zero-Order waveplates. And, a compensator can comprise more than two Zero-Order waveplate and/or effectively Zero-Order waveplates. FIGS. 9g1 and 9j, for instance, demonstrate in dashed lines the presence of additional Zero-Order waveplate and/or effectively Zero-Order waveplates. It is specifically noted that the dashed lines in FIG. 9g1 can represent a true single plate Zero-Order waveplate and the dashed lines in FIG. 9j an effectively Zero-Order waveplate. For instance, in FIG. 9j, the dashed lines can be an effective Zero-Order waveplate constructed from plates similar to (MOA1) and (MOB1). Also, the dashed lines in FIG. 9g1 can be interpreted represent a single Zero-Order waveplate similar to (MOA) in FIG. 9j, by assuming deletion of one dashed line. The Claims are to be understood in light of this disclosure.

A preferred disclosed invention embodiment as shown in FIG. 1b comprises a compensator means (C) which is selected from the group consisting of:
  comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;
  comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

Further, essentially any Compensator which can be placed into a beam of electromagnetic radiation can be applied, such as those disclosed in Claim 9 of U.S. Pat. No. 5,872,630, (which 630 patent is incorporated by reference hereinto):

Berek-type;
Non-Berek-type;
Zero Order;
Zero Order comprising a plurality of plates;
Rhomb;
Polymer;
Achromatic Crystal; and
Psuedo-Achromatic.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 9k1-9q demonstrate additional compensators which can be applied in the present invention.

FIG. 9k1 shows that the first additional present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped, element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 9k1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughout. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

FIG. 9k2 shows a variation (3') on FIG. 9k1, wherein the first triangular shaped element is replaced by two rotatable reflecting means, identified as (OS1') and (OS2'). This modification allows user adjustment so that the locus of an entering electromagnetic beam (LB') exits undeviated and undisplaced from an entering electromagnetic beam (LB).

Figure 9L:
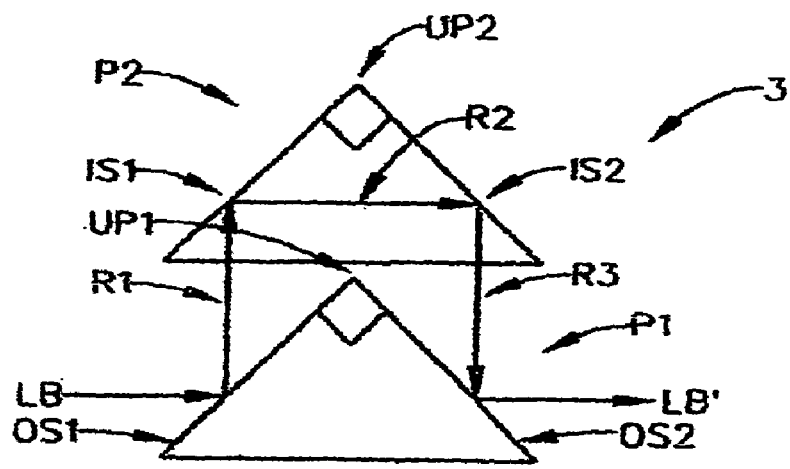
Figure 9L:
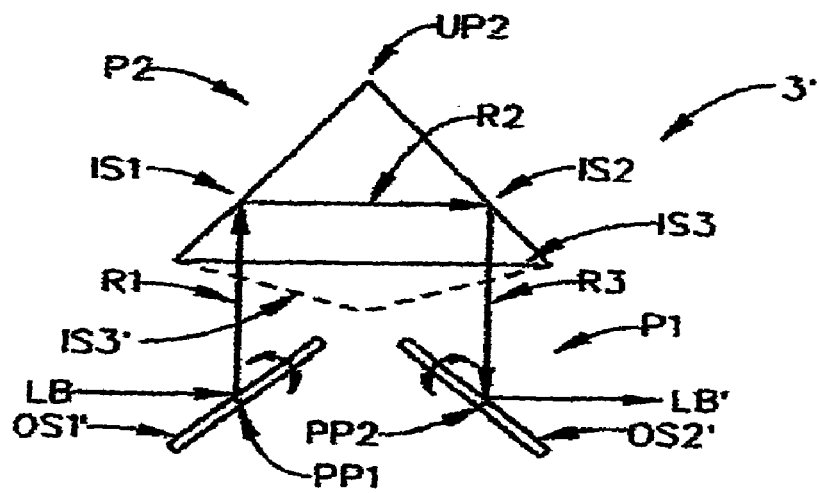
Figure 9L:
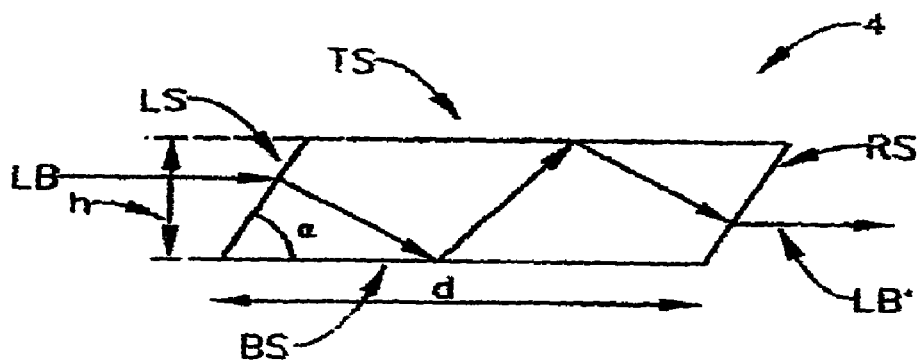

FIG. 9l shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(α)), where alpha (α) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha (α) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

$$\frac{d}{h} = 2 - \tan(\phi), \text{ where } \phi = \alpha + \sin^{-1}\left(\frac{\sin(90 - \alpha)}{n}\right)$$

Figure 9M:
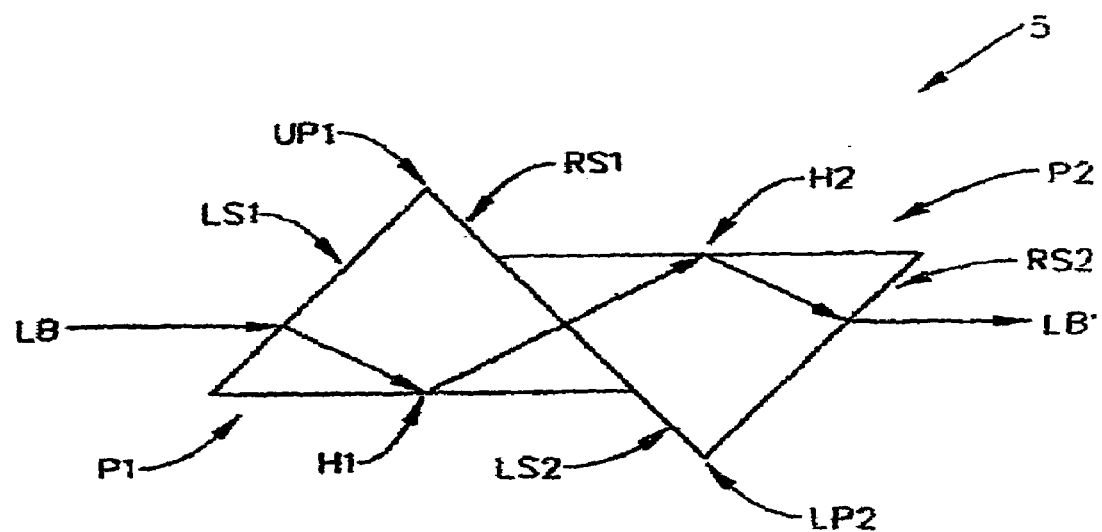

FIG. 9m shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 9N:
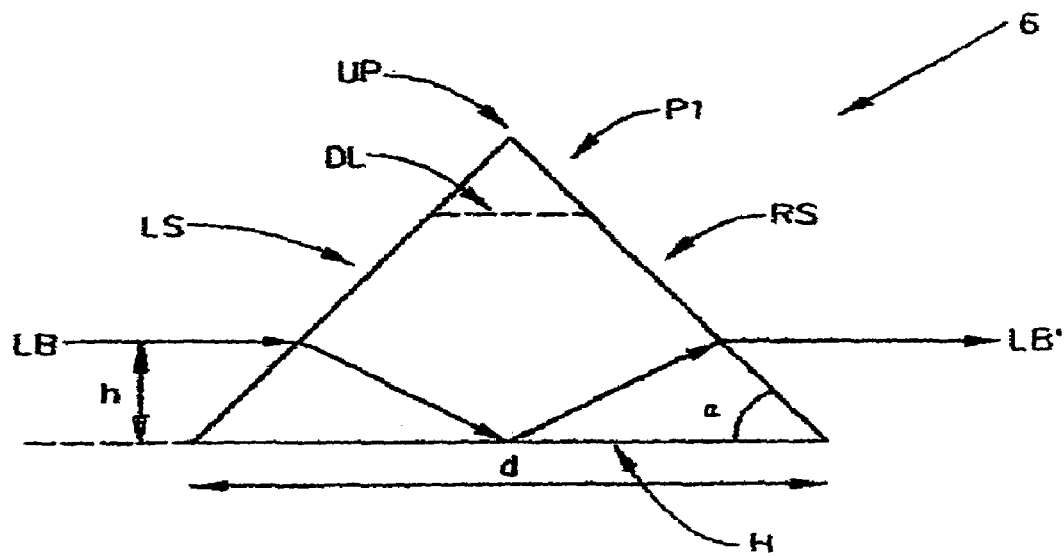

FIG. 9n shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 9n retarder system (6) is typically an isosceles prism which is available off-the-shelf with an angle alpha ( ) of forty-five

(45) degrees. As long as the input electromagnetic beam (LB) height (h) is chosen in accordance with the formula:

in conjunction with the index of refraction (n) of the material from which the retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

Figure 9Q:
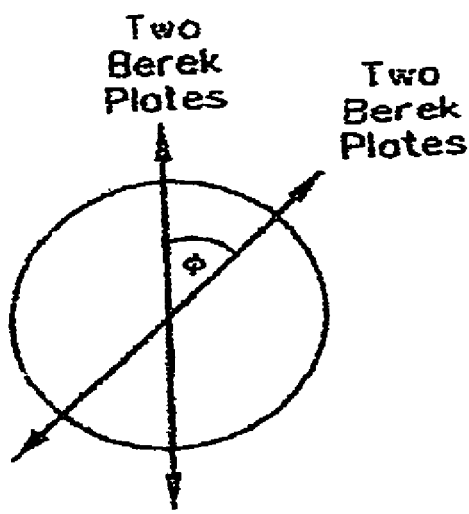
Figure 9Q:
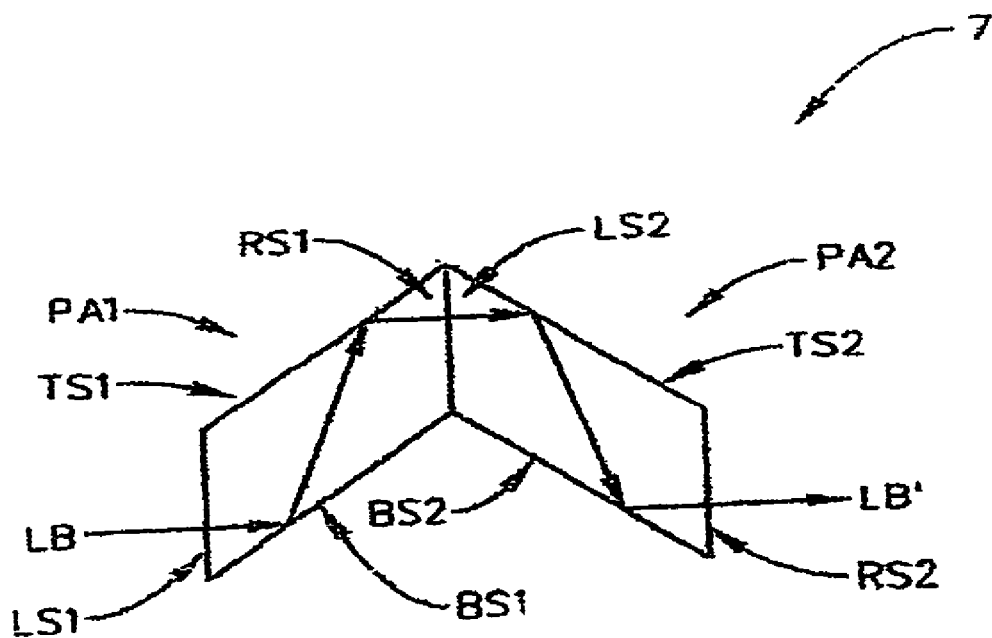

FIG. 9q shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 9o1 shows that the sixth additional present invention retarder system (8) comprises first (BK1) and second (BK2) Berek-type retarders which each have an optical axes essentially perpendicular to a surface thereof. As shown by FIG. 9o2, each of said first (BK1) and second (BK2) Berek-type retarders can have fast axis which are oriented other than parallel to one another, but for the presently described retarder system it is assumed that the fast axes are aligned, (ie. an angle PHI ( ) of zero (0.0) degrees exists between fast axes of the two Berek-type (BK1) and (BK2) plates in FIG. 9o1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately hal of achieved retardance. This insensitivity results because if the input electromagnetic beam is slightly changed, one of said plates will contribute slightly more (less), but the second slightly less (more) retardance because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 9o2 offset angle PHI ($\phi$) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 9p1 serves as the pictorial reference for the eighth additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 9p2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth additional present invention retarder system (11) is also pictorially represented by FIG. 9p1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different.

Now, and very importantly, even though the Invention disclosed in this Specification is a Rotating Compensator Material System Investigation System which is Spectroscopic, (ie. simultaneously operates on a number of Wavelengths in a Beam containing many Electromagnetic Wavelengths, over a range of, for instance, 190-1700 nanometers), a Compensator Means (C) (C') utilized therein can provide a Retardance which varies with Wavelength and still be usable. A Compensator Means (C) (C') does however, typically, have to be of a nature to allow passage of a Polychromatic Electromagnetic Beam therethrough without causing significant Attenuation, Deviation or Displacement in the Direction of Propagation thereof. Particularly as regards Deviation and Displacment, if this is not the case, difficult to compensate complexities are caused in Detector Elements (DE's) containing Photo Array Detector System (DET) Detector Element Output Signals.

The reason a Spectroscopic Ellipsometer can operate with a Compensator Means (C) (C') that does not provide a Constant Ninety (90) Degree Retardance over a range of Wavelengths, (which would constitute Ideal Characteristics), is that a Regression based Calibration Procedure utilized, (see the Disclosure of the Invention Section of this Specification), provides Wavelength dependent Compensation effecting values for Calibration Parameters as required in a developed Mathematical Model of the Rotating Compensator Material System Investigation System, (ie./eg. Rotating Compensator Spectroscopic Ellipsometer). As better described in the Disclosure of the Invention Section of this Disclosure, the Inventors develop a Calibration Parameter Containing Mathematical Model of the Rotating Compensator Material System Investigation System by, for instance, utilizing Matrix Representations for various System Components involved, then multiplies out the Matrices in an appropriate order to provide a Transfer Function. This applies for all Wavelengths monitored by a Detector Elements (DE's) containing Photo Array Detector System (DET) Detector Element (DE). Next, Data Set(s) are Experimentally obtained as a function of wavelength and typically as a function of various settings of the Polarizer Means (P) or Analyzer Means (A), (or both could be rotated to various positions), while a Compensator Means (C) rotates at, typically though not necessarily, Twenty (20) to Thirty (30) Hz. Other rotation speeds can be utilized and if two Compensator Means (C) (C') are present one or both can be caused to rotate, and if both are caused to rotate, as mentioned infra herein, they can be caused to rotate at the same, or different, speeds. (Note that Data Set(s) could also be achieved utilizing variation of Angle-of-Incidence of a Beam of Polychromatic Radiation with respect to a Material System under investigation). Calibration Parameters in the Mathematical Model are then evaluated by, typically, Mean-Square-Error based Regression onto the Data Set(s). It is also possible to effectively find Calibration Parameter containing Mathematical Expressions for Coefficients of Mathematical Series, (eg. Fourier Series), which comprise the Mathematical Model Transfer Function, and calculate Numerical Values for the Coefficients from the Data Set(s), then effectively perform Regression of said Calibration Parameter containing Mathematical Expressions for Coefficients of Mathematical Series Transfer Function onto said Numerical Values for the Coefficients from the Data Set(s). It is emphsized that a single Two-Dimensional Data Set has been found sufficient to allow excellent Calibration results to be achieved. Said Two-Dimensional Data Set typically is Intensity vs. Wavelength, and Polarizer Means or Analyzer Means Azimuthal Rotation Angle settings. In addition, said Two-Dimensional Data Set can be obtained from a Rotating Compensator Material System Investigation System oriented so that a Polychromatic Beam of Electromagnetic Radiation interacts with a Material System, (ie. the "Sample Present" Mode—see FIGS. 1a, 1b, 3, 4, and 5)), or such that said Polychromatic Beam of Electromagnetic Radiation passes through the Rotating Compensator Material System Investigation System without interacting with a Material System, other than a Material System, comprised of "Open Atmosphere".

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

The invention claimed is:

1. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system;
after said stage for supporting a material system; and
both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

said spectroscopic rotating compensator material system investigation system being further characterized by the presence of at least one combined spatial filter and relay system positioned before and/or after said stage for supporting a material system, wherein said spatial filter causes a polychromatic beam of electromagnetic radiation directed thereat to pass therethrough and exit therefrom as an effective point source, and wherein said relay system comprises at least one reflective concave surface and at least one reflective convex surface.

2. A spectroscopic rotating compensator material system investigation system as in claim 1, in which the at least one combined spatial filter and relay system comprises:
a) an aperture;
b) a flat mirror;
c) a concave spherical mirror having at least one concave spherical surface; and
d) a convex spherical mirror having at least one convex spherical surface;
said elements being arranged such that electromagnetic radiation from said aperture is caused to approach the flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects as a converging beam of electromagnetic radiation.

3. A spectroscopic rotating compensator material system investigation system as in claim 2, in which the at least one combined spatial filter and relay system which further comprises a second flat mirror positioned to intercept and reflect electromagnetic radiation reflected from said second location of said concave surface of said concave spherical mirror as a converging beam of electromagnetic radiation.

4. A spectroscopic rotating compensator material system investigation system as in claim 1, in which the at least one combined spatial filter and relay system comprises five elements:
a) an aperture;
b) a first flat mirror;
c) a concave spherical mirror having at least one concave spherical surface;
d) a convex spherical mirror having at least one convex spherical surface; and
e) a second flat mirror;
said elements being arranged such that electromagnetic radiation from said aperture is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror positioned to intercept and reflect electromagnetic radiation reflected from said second location of said concave surface of said concave spherical mirror as a converging beam of electromagnetic radiation.

5. A spectroscopic rotating compensator material system investigation system as in claim 4 in which the combined spatial filter and relay system provides that electromagnetic radiation from said aperture is caused to approach the first flat mirror at a 45 degree angle, and reflect from said second flat mirror at a 45 degree angle.

6. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system;
after said stage for supporting a material system; and
both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

said spectroscopic rotating compensator material system investigation system being further characterized by the presence of first and second relay systems positioned before and after said stage for supporting a material system, respectively;

said first and second relay systems, each comprising four elements:
  a) a first flat mirror;
  b) a concave spherical mirror having at least one concave spherical surface;
  c) a convex spherical mirror having at least one convex spherical surface; and
  d) a second flat mirror;

said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror positioned to intercept and reflect electromagnetic radiation reflected from said second location of said concave surface of said concave spherical mirror as a converging beam of electromagnetic radiation;

said material system being positioned between said first and second relay systems;

said first relay system being positioned to relay electromagnetic radiation from the source thereof, which passes through an aperture, and direct it onto a surface of said material system at an oblique angle of incidence, and said second relay system being positioned to receive electromagnetic radiation reflected from the material system and pass it on to said detector;

the propagation direction of electromagnetic radiation entering and exiting each of said first and second relay systems being substantially unchanged by passing therethrough;

said system being further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

7. A spectroscopic rotating compensator material system investigation system for investigating a material system as in claim 6 which further comprises at least one selection from the group consisting of:
  a) a fiber optic between said source and material system; and
  b) a fiber optic between said material system and detector.

8. A spectroscopic rotating compensator material system investigation system for investigating a material system as in claim 7 which further comprises at least two compensators between said source and detector.

9. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
  before said stage for supporting a material system;
  after said stage for supporting a material system; and
  both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

said spectroscopic rotating compensator material system investigation system being further characterized by the presence of:

first and second relay systems, each thereof comprising four elements:
  a) a first flat mirror;
  b) a concave spherical mirror having at least one concave spherical surface;
  c) a convex spherical mirror having at least one convex spherical surface; and
  d) a second flat mirror;

said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects onto said second flat mirror positioned to intercept and reflect electromagnetic radiation reflected from said second location of said concave surface of said concave spherical mirror as a converging beam of electromagnetic radiation;

said first and second relay systems being positioned on the same side of the material system;

the propagation direction of electromagnetic radiation entering and exiting each of said first and second relay systems being substantially unchanged by passing therethrough;

said system being further characterized in that a plane formed by the locus of the electromagnetic radiation passing through the first relay system is oriented 90 degrees to a plane formed by the locus of the electromagnetic radiation passing through the second relay system, the purpose being to minimize effects of said first and second relay systems on a polarization state of said electromagnetic radiation which passes through both thereof.

10. A spectroscopic rotating compensator material system investigation systemystem for investigating a material system as in claim 9 which further comprises at least one selection from the group consisting of:
  a) a fiber optic between said source and material system; and
  b) a fiber optic between said material system and detector.

11. A spectroscopic rotating compensator material system investigation system for investigating a material system as in claim 10 which further comprises at least two compensators between said source and detector.

12. A spectroscopic rotating compensator material system investigation system for investigating a material system as in claim 2 which further comprises a coating on at least one of the concave, convex and flat mirrors which changes the intensity vs. wavelength plot of a reflected electromagnetic beam relative to an incident beam.

13. A spectroscopic rotating compensator material system investigation system for investigating a material system as in claim 3 which further comprises a coating on at least one at the concave, convex and flat mirrors which changes the intensity vs. wavelength plot of a reflected electromagnetic beam relative to an incident beam.

14. A spectroscopic rotating compensator material system investigation system for investigating a material system as in claim 4 which further comprises a coating on at least one of the concave, convex, first flat and second flat mirrors which changes the intensity vs. wavelength plot of a reflected electromagnetic beam relative to an incident beam.

15. A spectroscopic rotating compensator material system investigation system for investigating a material system as in claim 6 which further comprises a coating on at least one of the concave, convex, first flat and second flat mirrors which changes the intensity vs. wavelength plot of a reflected electromagnetic beam relative to an incident beam.

16. A spectroscopic rotating compensator material system investigation system for investigating a material system as in claim 9 which further comprises a coating on at least one of the concave, convex, first flat and second flat mirrors which changes the intensity vs. wavelength plot of a reflected electromagnetic beam relative to an incident beam.

17. A spectroscopic rotating compensator material system investigation system for investigating a material system as in claim 1, in which said aperture hole is actually or effectively non-circular.

18. A spectroscopic rotating compensator material system investigation system for investigating a material system as in claim 2, in which said aperture is actually or effectively non-circular.

19. A spectroscopic rotating compensator material system investigation system for investigating a material system as in claim 4, in which said aperture is actually or effectively non-circular.

20. A spectroscopic rotating compensator material system investigation system for investigating a material system as in claim 6, in which said aperture is actually or effectively non-circular.

21. A spectroscopic rotating compensator material system investigation system for investigating a material system as in claim 9, in which said aperture is actually or effectively non-circular.

22. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
 before said stage for supporting a material system;
 after said stage for supporting a material system; and
 both before and after said stage for supporting a material system;
such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

said spectroscopic rotating compensator material system investigation system being further characterized by, between said source of a polychromatic beam and said detector, the presence of:
a relay system comprising three elements:
 a) a flat mirror;
 b) a concave spherical mirror having at least one concave spherical surface;
 c) a convex spherical mirror having at least one convex spherical surface;
said elements being arranged such that electromagnetic radiation is caused to approach the flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror from which it reflects as a converging beam of electromagnetic radiation; said system being further characterized by the presence of an aperture present prior to said flat mirror, through which aperture said beam of electromagnetic radiation passes before interacting with said flat mirror, and from which aperture said polychromatic beam of electromagnetic radiation exits as an effective point source.

23. A spectroscopic rotating compensator material system investigation system for investigating a material system as in claim 22 which further comprises at least one selection from the group consisting of:
 a) a fiber optic between said source and material system; and
 b) a fiber optic between said material system and detector.

24. A spectroscopic rotating compensator material system investigation system for investigating a material system as in claim 22 which further comprises a coating on at least one of the concave, convex, and flat mirror which changes the intensity vs. wavelength plot of a reflected electromagnetic beam relative to an incident beam.

25. A spectroscopic rotating compensator material system investigation system for investigating a material system as in claim 22, in which said aperture is actually or effectively non-circular.

26. A spectroscopic rotating compensator material system investigation system as in claim 1 in which the rotating compensator is of a type selected from the group consisting of:
 Berek-type with optical axis essentially perependicular to a surface thereof;
 non-Berek-type with an optical axis essentially parallel to a surface thereof;
 zero-order wave plate;
 zero-order waveplate constructed from two multiple order waveplates;

a sequential plurality of zero-order waveplates, each constructed each from a plurality of multiple order waveplates;
rhomb;
polymer;
achromatic crystal; and
pseudo-achromatic;
and in which said compensator provides retardance within a range of thirty (30.0) to less than one-hundred-thirty-five (135) degrees over a range of wavelengths defined by a selection from the group consisting of:
a) minimum wavelength is less than/equal to one-hundred-ninety (190) and maximum wavelength greater than/equal to seventeen-hundred (1700) nanometers;
b) minimum wavelength is less than/equal to two-hundred-twenty (220) and maximum wavelength MAXW greater than/equal to one-thousand (1000) nanometers;
c) within a range of wavelengths defined by a maximum wavelength (MAXW) and a minimum wavelength (MINW) range where (MAXW)/(MINW) is at least four-and-one-half (4.5);
or said compensator provides retardance within a range of seventy-five (75.0) to less than one-hundred-thirty-five (135) degrees over a range of wavelengths defined by a selection from the group consisting of:
a) between one-hundred-ninety (190) and seven-hundred-fifty (750) nanometers;
b) between two-hundred-forty-five (245) and nine-hundred (900) nanometers;
c) between three-hundred-eighty (380) and seventeen-hundred (1700) nanometers;
d) within a range of wavelengths defined by a maximum wavelength (MAXW) and a minimum wavelength (MINW) wherein the ratio of (MAXW)/(MINW) is at least one-and-eight-tenths.

27. A spectroscopic rotating compensator material system investigation system as in claim 1, in which the rotating compensator comprises a selection from the group consisting of:
comprised of a combination of at least two zero-order waveplates, said zero-order waveplates and having their respective fast axes rotated to a position offset from zero or ninety degrees with respect to one another;
comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates and in said first effective zero-order waveplate;
comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order wave plates in said second effective zero-order wave plate being rotated to a position away from zero or ninety degrees with respect to the fast axes of the multiple order waveplates and in said first effective zero-order waveplate; and
comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate;
Berek-type with optical axis essentially perependicular to a surface thereof;
non-Berek-type with an optical axis essentially parallel to a surface thereof;
zero-order wave plate;
zero-order waveplate constructed from two multiple order waveplates;
a sequential plurality of zero-order waveplates, each constructed each from a plurality of multiple order waveplates;
rhomb;
polymer;
achromatic crystal; and
pseudo-achromatic;
and in which said compensator provides retardance within a range of thirty (30.0) to less than one-hundred-thirty-five (135) degrees over a range of wavelengths defined by a selection from the group consisting of:
a) minimum wavelength is less than/equal to one-hundred-ninety (190) and maximum wavelength greater than/equal to seventeen-hundred (1700) nanometers;
b) minimum wavelength is less than/equal to two-hundred-twenty (220) and maximum wavelength MAXW greater than/equal to one-thousand (1000) nanometers;
c) within a range of wavelengths defined by a maximum wavelength (MAXW) and a minimum wavelength (MINW) range where (MAXW)/(MINW) is at least four-and-one-half (4.5);
or said compensator provides retardance within a range of seventy-five (75.0) to less than one-hundred-thirty-five (135) degrees over a range of wavelengths defined by a selection from the group consisting of:
a) between one-hundred-ninety (190) and seven-hundred-fifty (750) nanometers;
b) between two-hundred-forty-five (245) and nine-hundred (900) nanometers;
c) between three-hundred-eighty (380) and seventeen-hundred (1700) nanometers;
d) within a range of wavelengths defined by a maximum wavelength (MAXW) and a minimum wavelength (MINW) wherein the ratio of (MAXW)/(MINW) is at least one-and-eight-tenths.

28. A spectroscopic rotating compensator material system investigation system comprising a source of a polychromatic beam of electromagnetic radiation, a first aperture, a second aperture, a fixed polarizer, a rotating compensator, a third aperture, a forth aperture, a fifth aperture, a stage for supporting a material system, a sixth aperture, a seventh aperture, an eighth aperture, a fixed analyzer, a ninth aperture, a substantially achromatic lens, an optical fiber and at least one detector system which comprises a dispersive element and a multiplicity of detector elements, there optionally being a UV filter present between said source of a polychromatic beam of electromagnetic radiation and said stage for supporting a material system;

such that when said spectroscopic rotating compensator material system investigation system is used to investigate a material system present on said stage for supporting a material system, said fixed analyzer and fixed polarizer are maintained essentially fixed in position and said rotating compensator is caused to continuously rotate while a polychromatic beam of electromagnetic radiation produced by said source of a polychromatic beam of electromagnetic radiation is sequentially caused to pass through said first aperture, second aperture, fixed polarizer, rotating compensator, third aperture, forth aperture, fifth aperture, said polychromatic beam of electromagnetic radiation then interact with a material system placed on said stage for supporting a material system and sequentially passing through said sixth aperture, seventh aperture, eighth aperture, fixed analyzer, ninth aperture, said substantially achromatic lens, enter said optical fiber and there via enter said detector system;

said spectroscopic rotating compensator material system investigation system being further characterized by the presence of at least one combined spatial filter and relay system positioned before and/or after said stage for supporting a material system.

29. A spectroscopic rotating compensator material system investigation system as in claim 28 in which the rotating compensator comprises a selection from the group consisting of:

comprised of a combination of at least two zero-order waveplates, said zero-order waveplates and having their respective fast axes rotated to a position offset from zero or ninety degrees with respect to one another;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple, order waveplates and in said first effective zero-order waveplate;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates and in said first effective zero-order waveplate; and comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate;

Berek-type with optical axis essentially perependicular to a surface thereof;

non-Berek-type with an optical axis essentially parallel to a surface thereof;

zero-order wave plate;

zero-order waveplate constructed from two multiple order waveplates;

a sequential plurality of zero-order waveplates, each constructed each from a plurality of multiple order waveplates;

rhomb;

polymer;

achromatic crystal; and pseudo-achromatic;

and in which said compensator provides retardance within a range of thirty (30.0) to less than one-hundred-thirty-five (135) degrees over a range of wavelengths defined by a selection from the group consisting of:

a) minimum wavelength is less than/equal to one-hundred-ninety (190) and maximum wavelength greater than/equal to seventeen-hundred (1700) nanometers;

b) minimum wavelength is less than/equal to two-hundred-twenty (220) and maximum wavelength MAXW greater than/equal to one-thousand (1000) nanometers;

c) within a range of wavelengths defined by a maximum wavelength (MAXW) and a minimum wavelength (MINW) range where (MAXW)/(MINW) is at least four-and-one-half (4.5);

or said compensator provides retardance within a range of seventy-five (75.0) to less than one-hundred-thirty-five (135) degrees over a range of wavelengths defined by a selection from the group consisting of:

a) between one-hundred-ninety (190) and seven-hundred-fifty (750) nanometers;

b) between two-hundred-forty-five (245) and nine-hundred (900) nanometers;

c) between three-hundred-eighty (380) and seventeen-hundred (1700) nanometers;

d) within a range of wavelengths defined by a maximum wavelength (MAXW) and a minimum wavelength (MINW) wherein the ratio of (MAXW)/(MINW) is at least one-and-eight-tenths.

30. A spectroscopic rotating compensator material system investigation system as in claim 28, in which:

said first aperture is a pinhole, through which a portion of the polychromatic beam of electromagnetic radiation passes, with a nominal internal diameter of between 100 and 600 microns;

said second aperture through which a portion of the polychromatic beam of electromagnetic radiation passes, has a nominal internal diameter has a nominal internal diameter of 3 to 3.5 millimeters;

said third aperture, through which a portion of the polychromatic beam of electromagnetic radiation passes, has an internal diameter has a nominal internal diameter of 3.5 millimeters;

said forth aperture, through which a portion of the polychromatic beam of electromagnetic radiation passes, has an internal diameter has a nominal internal diameter of 3.75 millimeters;

said fifth aperture, through which a portion of the polychromatic beam of electromagnetic radiation passes, has an internal diameter has a nominal internal diameter of 4.8 millimeters;

said sixth aperture, through which a portion of the polychromatic beam of electromagnetic radiation passes, has an internal diameter has a nominal internal diameter of 4.8 millimeters;

said seventh aperture, through which a portion of the polychromatic beam of electromagnetic radiation passes, has an internal diameter has a nominal internal diameter of 3.75 millimeters;

an eighth aperture, through which a portion of the polychromatic beam of electromagnetic radiation passes, has an internal diameter has a nominal internal diameter of 3.5 millimeters;

said ninth aperture, through which a portion of the polychromatic beam of electromagnetic radiation passes, has an internal diameter has an adjustible internal diameter.

31. A spectroscopic ellipsometer or polarimeter system as in claim 1 in which the multiplicity of detector elements are arranged in a selection from the group consisting of:
   one-dimensional array;
   two-dimensional array; and
   three-dimensional array.

32. A spectroscopic ellipsometer or polarimeter system as in claim 9 in which the multiplicity of detector elements are arranged in a selection from the group consisting of:
   one-dimensional array;
   two-dimensional array; and
   three-dimensional array.

33. A spectroscopic ellipsometer or polarimeter system as in claim 28 in which the multiplicity of detector elements are arranged in a selection from the group consisting of:
   one-dimensional array;
   two-dimensional array; and
   three-dimensional array.

* * * * *